(12) United States Patent
Zhao et al.

(10) Patent No.: US 9,040,677 B2
(45) Date of Patent: *May 26, 2015

(54) TRANSCRIPTION ACTIVATOR-LIKE EFFECTOR ASSEMBLY

(71) Applicant: SIDANSAI Biotechnology CO., LTD, Shanghai (CN)

(72) Inventors: Jinlong Zhao, Shanghai (CN); Zhao Wu, Shanghai (CN)

(73) Assignee: SIDANSAI Biotechnology CO., LTD, Shanghai (CN)

( * ) Notice: Subject to any disclaimer, the term of this patent is extended or adjusted under 35 U.S.C. 154(b) by 31 days.

This patent is subject to a terminal disclaimer.

(21) Appl. No.: 13/965,469

(22) Filed: Aug. 13, 2013

(65) Prior Publication Data

US 2014/0073014 A1    Mar. 13, 2014

(30) Foreign Application Priority Data

Sep. 12, 2012  (CN) .......................... 2012 1 0336604

(51) Int. Cl.
| | | |
|---|---|---|
| *C07H 21/00* | (2006.01) |
| *C12Q 1/68* | (2006.01) |
| *C12P 19/34* | (2006.01) |
| *C12N 15/66* | (2006.01) |
| *C12N 15/10* | (2006.01) |
| *C12N 15/64* | (2006.01) |

(52) U.S. Cl.
CPC . *C12P 19/34* (2013.01); *C12Q 1/68* (2013.01); *C07H 21/00* (2013.01); *C12N 15/66* (2013.01); *C12N 15/102* (2013.01); *C12N 15/64* (2013.01)

(58) Field of Classification Search
CPC .................................. C12Q 1/68; C07H 21/00
USPC ........................................... 435/6.1; 536/25.3
See application file for complete search history.

(56) References Cited

U.S. PATENT DOCUMENTS 8,748,134 B2 *   6/2014   Zhao et al. .................... 435/91.2

OTHER PUBLICATIONS

Engler et al, "Golden Gate Shuffling: A One-Pot DNA Shuffling Method Based on Type IIs Restriction Enzymes", PLoS One, May 2009, vol. 4, Issue 5, 9 pgs.
Geibler et al, "Transcriptional Activators of Human Genes with Programmable DNA-Specificity", PLoS One, May 2011, vol. 6, Issue 5, 7 pgs.
Huang et al, "Heritable Gene Targeting in Zebrafish Using Customized TALENs", Correspondence, Nature Biotechnology, Aug. 2011, vol. 29, No. 8, 2 pgs.
Kim et al, "A Library of TAL Effector Nucleases Spanning the Human Genome", Nature Biotechnology, Mar. 2013, vol. 31, No. 3, 9 pgs.
Li et al, "Rapid and Highly Efficient Construction of TALE-based Transcriptional Regulators and Nucleases for Genome Modification", Plant Mol Biol, Mar. 2012, 78(405), 16 pgs.
Morbitzer et al, "Regulation of Selected Genome Loci using De Novo-Engineered Transcription Activator-Like Effector (TALE)—Type Transcription Factors", PNAS, Dec. 2010, vol. 107, No. 50, 6 pgs.
Sander et al, "Targeted Gene Disruption in Somatic Zebrafish Cells using Engineered TALENs", Nat Biotechnol., 29 (8), Feb. 2005, 6 pgs.
TAL Effectors Resources, "Concise TALE Construction Protocol (V.20120425)", Adapted from Sanjana et al, Nature Protocols 2011, 2 pgs.
Weber et al, "Assembly of Designer TAL Effectors by Golden Gate Cloning", PLoS One, May 2011, vol. 6, No. 5, 5 pgs.
Zhang et al, "Programmable Sequence-Specific Transcriptional Regulation of Mammalian Genome Using Designer TAL Effectors", Nat Biotechnol, Feb. 2011, 29(2), 11 pgs.

* cited by examiner

*Primary Examiner* — Ardin Marschel
(74) *Attorney, Agent, or Firm* — Tian IP & Technology, LLC.

(57) ABSTRACT

Described herein are techniques for assembling a polynucleotide encoding a transcription activator-like effector nucleases (TALEN). The techniques ligate and digest necessary modules for a TALEN assembly in one reactor or system. Methods and Kits for generating a TALEN are also described.

16 Claims, 8 Drawing Sheets

TRANSCRIPTION ACTIVATOR-LIKE EFFECTOR ASSEMBLY

CROSS REFERENCE TO RELATED PATENT APPLICATIONS

This application claims priority to Chinese Patent Application No. 201210336604.4, filed on Sep. 12, 2012, entitled "A DNA library and a method for transcription activator-like effector nuclease plasmid assembly," which is hereby incorporated by reference in its entirety.

SEQUENCE LISTING

The Sequence Listing associated with this application is provided in text format in lieu of a paper copy, and is hereby incorporated by reference into the specification. The name of the text file containing the Sequence Listing is Sequence_listing_5132-0002US.txt. The text file is about 27 KB, was created on Aug. 5, 2013, and is being submitted electronically via EFS-Web.

TECHNICAL FIELD

This disclosure relates to genome engineering. More specifically, the disclosure relates to designed transcription activator-like effector assemblies.

BACKGROUND

Target genome engineering is desirable for many scientists. By deleting or inserting a designed and specific nucleotide sequence in an endogenous genome, scientists can generate various animal models for performing fundamental biological research and studying mechanisms of disease. In addition, scientists can create transgenic animals to produce biological compositions and/or components, which may be difficult to obtain from other resources. However, it is challenging to perform targeted and specific genome modifications using traditional techniques. The traditional techniques rely on random fragment exchanges of homologous chromosomes in natural cellular processes. Therefore, the efficiency for the traditional techniques is low (e.g., $10^{-6}$-$10^{-8}$ as a successfully rate). Because of this low efficiency, these techniques are generally applied in mice rather than other animal models (e.g., large mammalians).

In 2009, two research groups identified a transcription activator-like effector (TALE) in plant pathogen *Xanthomonas*, which modulates host gene functions by binding specific sequences within gene promoters. The TALE related techniques helped scientists develop an easier method for targeted genome engineering. This technique fuses TALE to FokI to generate a transcription activator-like effector nuclease (TALEN). In general, TALEs include tandem-like and nearly identical monomers (i.e., repeat domains), flanked by N-terminal and C-terminal sequences. Each monomer contains 34 amino acids, and the sequence of each monomer is highly conserved. Only two amino acids per repeat (i.e., residues $12^{th}$ and $13^{th}$) are hypervariable, and are also known as repeat variable di-residues (RVDs). The RVDs determines the nucleotide-binding specificity of each TALE repeat domain.

TALE related techniques have increased the efficiency and usages of genome engineering, and make the genome engineering more convenient. However, assembling ten to twenty highly conserved DNA modules into a vector is a big challenge.

BRIEF DESCRIPTION OF THE DRAWINGS

The detailed description is described with reference to the accompanying figures.

DETAILED DESCRIPTION

Figure 1A:
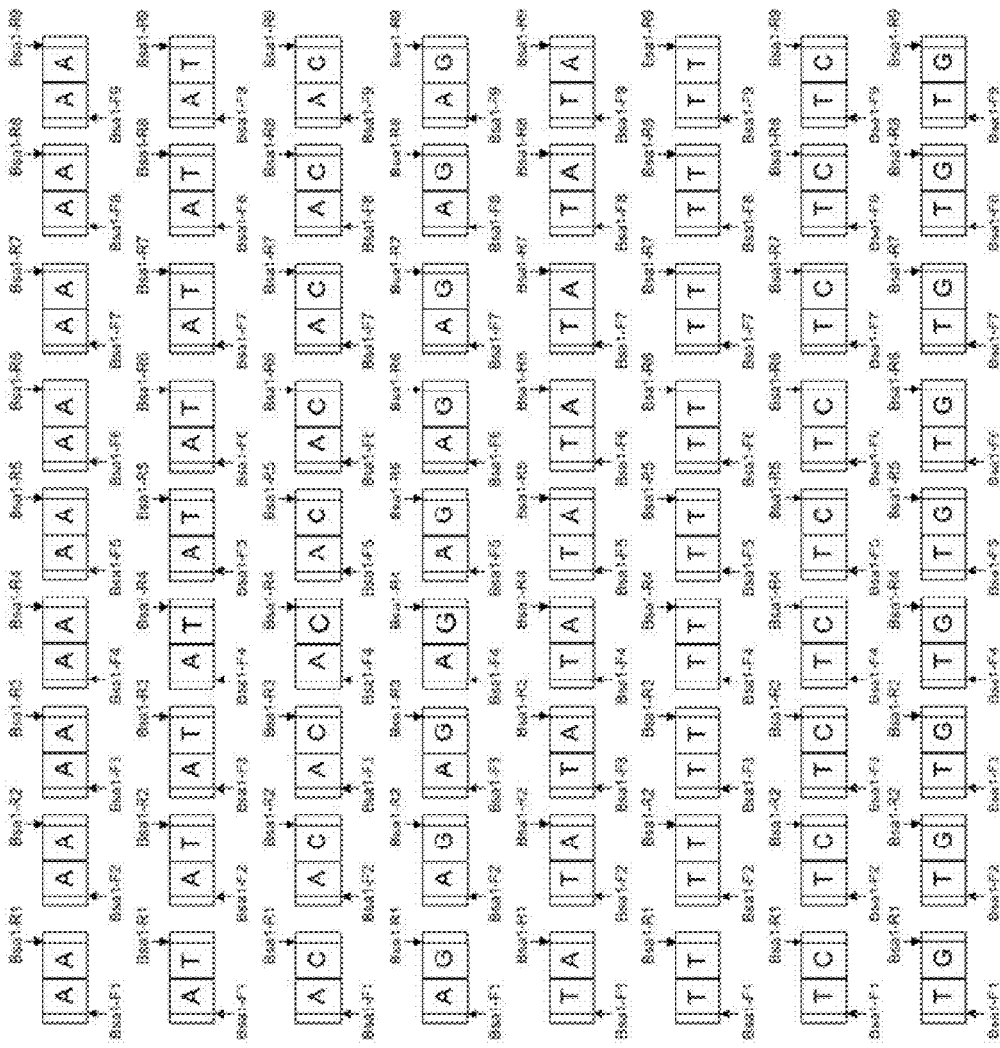
FIG. 1A is a diagram showing an exemplary DNA library including dimer repeat modules.

Various methods have been developed for assembling TALENs, such as chemical synthesis, two-step molecular cloning, and one-step molecular cloning. However, any of these methods has its own drawback. For example, although highly-repeated DNA sequences may be chemically synthesized, the cost is high and the outcome is hardly predictable. Also, two-step molecular cloning is also expensive, considering the cost of materials and sequencing, as well as time consuming. As for one-step molecular cloning, under current techniques, the maximum number of DNA modules encoding a TALEN is 14 using dimer modules. However, although natural TALEs may include 12-23 repeat modules, designed TALEs are generally more than 14 repeat modules. Therefore, to generate a TALEN including more than 14 repeat modules, current techniques require multiple steps for enzyme digestion, purifications, and ligation. This not only limits the scope of use of TALENs related genome engineering, but also affects TALENs specificity. In addition, it is a challenge to properly store intermediate products (e.g., digested DNA segments and a tail of single strand). In sum, assembling a polynucleotide encoding a TALE including more than 14 repeat domains in a single cloning reaction has not been accomplished.

Methods involving conventional molecular biology techniques are described herein. Such techniques are general known in the art unless otherwise specified in this disclosure. These techniques include PCR amplification and detection, cell transfection, cell culture, and detection techniques.

Embodiments of this disclosure relate to a transcription activator-like effector nuclease (TALEN) assembly library and/or kit, which can be used for ligation of multiple repeat DNA modules encoding TALENs. In certain embodiments, the number of the multiple repeat modules is greater than 14.

In certain related embodiments, the TAL assembly library may include 16 sets, and each set includes n dimers, wherein n is an integer. In some embodiments, the TAL assembly library may include 4 sets, and each set includes m monomers, wherein m is an integer and is not greater than n. As defined herein, a DNA module for TALE assembles may encode a single nucleotide recognition domain, and is therefore referred as a monomer DNA module (i.e., monomer). The single nucleotide recognition domain includes two amino acids recognizing one of A, T, C, and G. In addition, a DNA module for TALE assembles may encode a double nucleotide recognition domain, and therefore is referred as a dimer DNA module (i.e., dimer), which includes amino acids that recognize one of AA, AT, AC, AG, TT, TA, TC, TG, CC, CA, CT, CG, GG, GA, GT, and GC. In some embodiments, a set of monomers or dimers may recognize the same single nucleotide and the same pair of nucleotides respectively.

In some embodiments, each dimer or monomer may contain a $1^{st}$ overhang and a $2^{nd}$ overhang that are generated from digestion of type II restriction endonucleases, such as BsaI, BsmB1, BsmA1, and BbsI. In some instances, the digestion and later ligation are performed using only BsaI. In certain embodiments, a sequence of the $2^{nd}$ overhang of a dimer (e.g., dimer i) may be complementary to a sequence of the $1^{st}$ overhang of a dimer that is located after and adjacent to the dimer i, wherein i is an integer greater than 1 but less than n. In certain embodiments, a sequence $2^{nd}$ overhang of a monomer (e.g., monomer j) may be complementary to a sequence $1^{st}$ overhang of a monomer that is located after and adjacent to the monomer j, wherein j is an integer greater than 1 but less than m.

Figure 5:
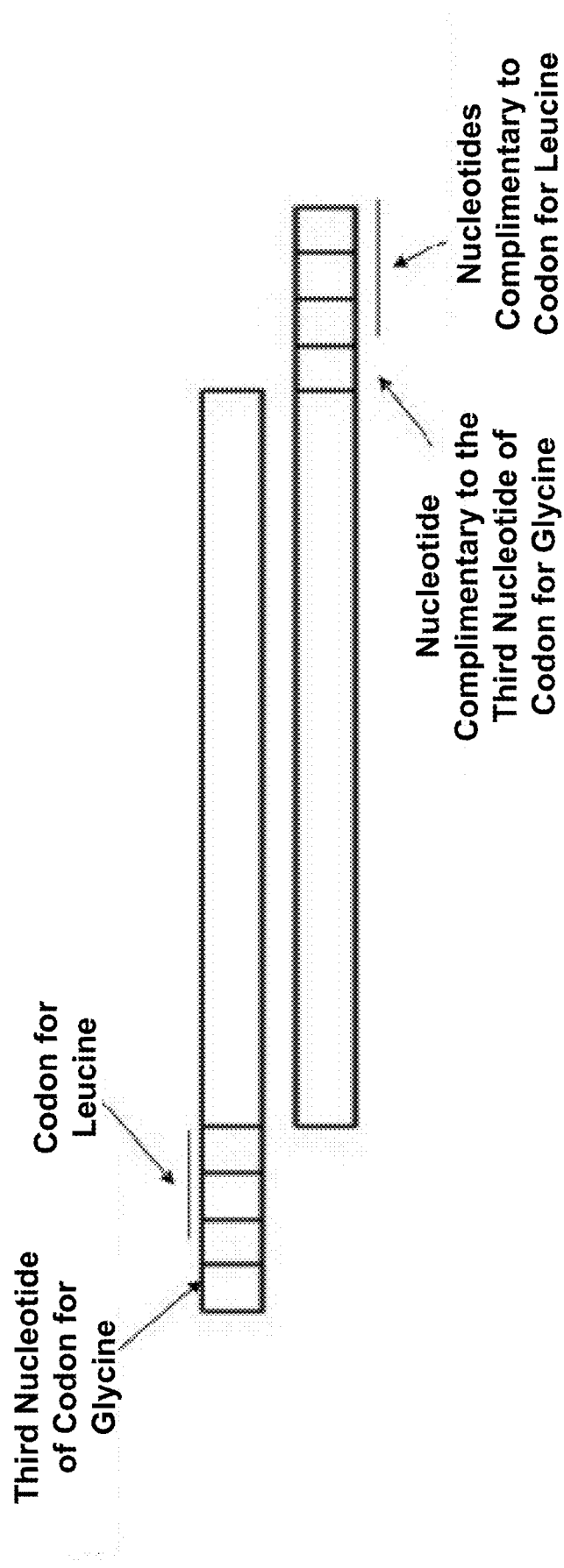
FIG. 5 is an exemplary process showing a TALE assembly.
Figure 6:
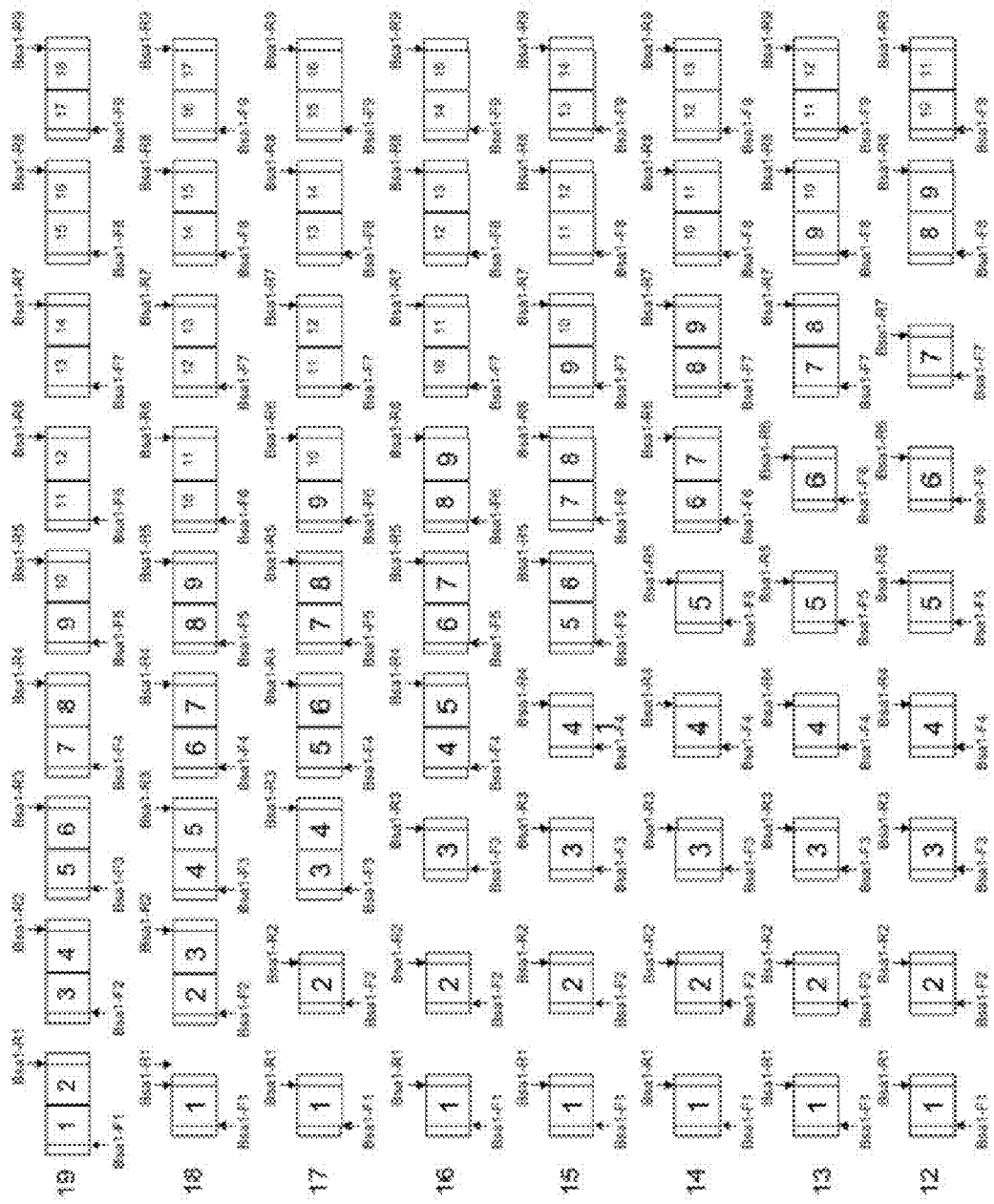
FIG. 6 is a diagram showing exemplary monomers and dimers for TALE assemblies.

For example, as illustrated in FIG. 5, there are four nucleotides at the overhang, from 5' to 3'. In this overhang, the $2^{nd}$ to $4^{th}$ nucleotides are a codon for Leu, and the first nucleotide in sense strand is the last nucleotide for a codon for Gly. In the antisense strand, the last two nucleotides are the first two nucleotides of a codon for Gly, while the first three nucleotides are complementary to a codon for Leu.

In some embodiments, dimers may be numbered as 1, . . . l, . . . and n, and monomers may be numbered as 1, j, . . . and m. For example, when n is not less than 7, more than 14 modules are assembled; when n is 9 and m is 7, 19 modules are assembled.

In some embodiments, given that DNA modules are not easy for storage or self-amplification, DNA modules may be inserted into a plasmid in a circular structure for better storage and amplification.

Embodiments of this disclosure also relate to a DNA library including multiple DNA segments each corresponding to a repeat domain of a TALE. In some embodiments, each DNA segment may contain a module component and one or more fusion components fused to another DNA segment. Each DNA segment may also have cutting sites of type II restriction endonucleases. Therefore, DNA segments may be flanked by a type II restriction endonuclease to obtain DNA modules for TALE assemblies. In certain embodiments, the DNA segments may be PCR amplification products or recombinant plasmids, such as pMD18-T, TOPO® plasmids, pUC19, and pUC18.

Embodiments of this disclosure also relate to methods for transcription activator-like effector nuclease plasmid assembly. In certain embodiments, the method may include identifying target gene sequences, and designing corresponding TALENs, such as repeat domains of a TALE. Based on repeat domains, multiple DNA segments may be selected from a DNA library. In these instances, in a single cloning reaction reactor, the multiple DNA segments, type II restriction endonucleases, DNA ligases, and TALE backbone vector (e.g., plasmids) may be mixed together to generate a polynucleotide encoding a TALEN. For example, the multiple DNA segments may be inserted into a backbone plasmid that contains a polynucleotide encoding a DNA restriction enzyme. The polynucleotides encoding TALENs may be purified by removing incomplete ligation products (e.g., linear DNA segments) using a plasmid-safe Deoxyribonuclease (DNase).

In some embodiments, individual DNA modules may be ligated to other DNA modules in an order. During ligations of a module to another module or a module to a plasmid, type II restriction endonucleases may not be able to cut additional nucleotides. In some embodiments, the multiple DNA segments (e.g., all DNA segments encoding a TALE), the backbone plasmids, the type II restriction endonucleases, and DNA ligases may be put in a single reactor to generate polynucleotides encoding TALENs, wherein digestion and ligation occur at substantially the same time. In certain embodiments, the type II restriction endonuclease may be BsaI, and the DNA ligase may be T4 ligase.

For example, a single ligation reactor or assembly reactor may include 40-200 ng plasmids, 20-200 DNA segments, 0.5-2 µl type II restriction endonuclease, 0.5-2 µl DNA ligase, 2 µl DNA ligation buffer, and double-distilled water (ddH$_2$O) to be added to reach a final volume of 20 µl. The ligation process may include 15 cycles: 37° C. for 5 min, 16° C. for 10 min, and followed by 80° C. for 10 min.

A polynucleotide sequence of a TALEN plasmid includes a DNA restriction enzyme, N-terminal and C-terminal may be set forth in any of SEQ ID NO. 41 and SEQ ID NO. 42. During the process, the TALEN backbone plasmid may be cut by type II restriction endonuclease to create a linear DNA segment with two overhangs. An overhang may be ligated to the $1^{st}$ overhang of a monomer j or dimer i; and the other overhang may be ligated to the $2^{nd}$ overhang of the monomer j or dimer i.

In some embodiments, incomplete products may be removed using Plasmid-Safe nucleases. The incomplete linear or linearized DNA segments reduce the ligation efficiency by recombination. In some instances, before transformation of generated TALENs, Plasmid-Safe™ ATP-Dependent DNase (Epicentre, cat no: E3105K) may be used to digest linear or linearized DNA segments to increase the ligation efficiency.

In certain embodiments, a designed TALEN may include 20 repeat domains, and thus a polynucleotide encoding the designed TALEN may be generated using 20 DNA modules from a DNA library for TALEN assembles. In certain embodiments, using appropriate primers, the DNA library for TALENs assembly may be obtained. The DNA library may contain multiple DNA modules (e.g., 172 modules). These DNA modules may be monomers each corresponding to a TALE recognition module recognizing one nucleotide, and/or dimers each corresponding to two TALE recognition modules recognizing two nucleotides. Each of the monomers and dimers contains type II restriction endonuclease cutting sites. By using this DNA library, enzyme digestion and ligation (e.g., 19-module ligation) may be performed in one reaction reactor or system, therefore avoiding purifications and additional ligation steps. This increases production efficiency, and thus improves TALE related techniques. In some embodiments, because DNA modules are plasmids or corresponding PCR products, certain risks (e.g., tail end damages and DNA degradations) are avoided. This simplifies TALEN generation procedures, and therefore reduces the cost.

In some embodiments, a polynucleotide encoding TALEN including 20 repeat domains may be assembled in a single reaction reactor or system. For example, an individual TALE repeat modules of these 20 repeat modules may identify each of 4 monomers (A, T, C, and G) or each of 16 dimers (AA, AT, AC, AG, TA, TT, TC, TG, CA, CT, CC, CG, GA, GT, GC, and GG). Therefore, RVDs of the TALE repeat module may be NI, NG, HD, and NN if the TALE repeat module identifies one nucleotide, or NI-NI, NI-NG, NI-HD, NI-NN, NG-NI, NG-NG, NG-HD, NG-NN, HD-NI, HD-NG, HD-HD, HD-NN, NN-NI, NN-NG, NN-HD, NN-NN if the TALE repeat module identifies two nucleotides. Exemplary sequences of polynucleotides encoding the TALE repeat modules are listed in Table 1.

TABLE 1

| Name | Sequence | SEQ ID |
|---|---|---|
| NI | CTGACCCCAGAGCAGGTCGTGGCAATCGCCTCCAACATTGGCGG GAAACAGGCACTCGAGACTGTCCAGCGCCTGCTTCCCGTGCTGTG CCAAGCGCACGGA | SEQ ID NO: 1 |
| NG | CTGACCCCAGAGCAGGTCGTGGCCATTGCCTCGAATGGAGGGGG CAAACAGGCGTTGGAAACCGTACAACGATTGCTGCCGGTGCTGT GCCAAGCGCACGGC | SEQ ID NO: 2 |
| HD | TTGACCCCAGAGCAGGTCGTGGCGATCGCAAGCCACGACGGAGG AAAGCAAGCCTTGGAAACAGTACAGAGGCTGTTGCCTGTGCTGT GCCAAGCGCACGGG | SEQ ID NO: 3 |
| NN | CTTACCCCAGAGCAGGTCGTGGCAATCGCGAGCAATAACGGCGG AAAACAGGCTTTGGAAACGGTGCAGAGGCTCCTTCCAGTGCTGT GCCAAGCGCACGGG | SEQ ID NO: 4 |
| NI-NI | CTGACCCCAGAGCAGGTCGTGGCAATCGCCTCCAACATTGGCGG GAAACAGGCACTCGAGACTGTCCAGCGCCTGCTTCCCGTGCTTTG TCAGGCACACGGCCTCACTCCGGAACAAGTGGTCGCAATCGCCTC CAACATTGGCGGGAAACAGGCACTCGAGACTGTCCAGCGCCTGC TTCCCGTGCTGTGCCAAGCGCACGGT | SEQ ID NO: 5 |
| NI-NG | CTGACCCCAGAGCAGGTCGTGGCAATCGCCTCCAACATTGGCGG GAAACAGGCACTCGAGACTGTCCAGCGCCTGCTTCCCGTGCTTTG TCAGGCACACGGCCTCACTCCGGAACAAGTGGTCGCCATTGCCTC GAATGGAGGGGGCAAACAGGCGTTGGAAACCGTACAACGATTG CTGCCGGTGCTGTGCCAAGCGCACGGT | SEQ ID NO: 6 |
| NI-HD | CTGACCCCAGAGCAGGTCGTGGCAATCGCCTCCAACATTGGCGG GAAACAGGCACTCGAGACTGTCCAGCGCCTGCTTCCCGTGCTTTG TCAGGCACACGGCCTCACTCCGGAACAAGTGGTCGCGATCGCAA GCCACGACGGAGGAAAGCAAGCCTTGGAAACAGTACAGAGGCT GTTGCCTGTGCTGTGCCAAGCGCACGGT | SEQ ID NO: 7 |
| NI-NN | CTGACCCCAGAGCAGGTCGTGGCAATCGCCTCCAACATTGGCGG GAAACAGGCACTCGAGACTGTCCAGCGCCTGCTTCCCGTGCTTTG TCAGGCACACGGCCTCACTCCGGAACAAGTGGTCGCAATCGCGA GCAATAACGGCGGAAAACAGGCTTTGGAAACGGTGCAGAGGCT CCTTCCAGTGCTGTGCCAAGCGCACGGT | SEQ ID NO: 8 |
| NG-NI | CTGACCCCAGAGCAGGTCGTGGCCATTGCCTCGAATGGAGGGGG CAAACAGGCGTTGGAAACCGTACAACGATTGCTGCCGGTGCTTTG TCAGGCACACGGCCTCACTCCGGAACAAGTGGTCGCAATCGCCTC CAACATTGGCGGGAAACAGGCACTCGAGACTGTCCAGCGCCTGC TTCCCGTGCTGTGCCAAGCGCACGGT | SEQ ID NO: 9 |
| NG-NG | CTGACCCCAGAGCAGGTCGTGGCCATTGCCTCGAATGGAGGGGG CAAACAGGCGTTGGAAACCGTACAACGATTGCTGCCGGTGCTTTG TCAGGCACACGGCCTCACTCCGGAACAAGTGGTCGCCATTGCCTC GAATGGAGGGGGCAAACAGGCGTTGGAAACCGTACAACGATTG CTGCCGGTGCTGTGCCAAGCGCACGGT | SEQ ID NO: 10 |
| NG-HD | CTGACCCCAGAGCAGGTCGTGGCCATTGCCTCGAATGGAGGGGG CAAACAGGCGTTGGAAACCGTACAACGATTGCTGCCGGTGCTTTG TCAGGCACACGGCCTCACTCCGGAACAAGTGGTCGCGATCGCAA GCCACGACGGAGGAAAGCAAGCCTTGGAAACAGTACAGAGGCT GTTGCCTGTGCTGTGCCAAGCGCACGGT | SEQ ID NO: 11 |
| NG-NN | CTGACCCCAGAGCAGGTCGTGGCCATTGCCTCGAATGGAGGGGG CAAACAGGCGTTGGAAACCGTACAACGATTGCTGCCGGTGCTTTG TCAGGCACACGGCCTCACTCCGGAACAAGTGGTCGCAATCGCGA GCAATAACGGCGGAAAACAGGCTTTGGAAACGGTGCAGAGGCT CCTTCCAGTGCTGTGCCAAGCGCACGGT | SEQ ID NO: 12 |
| HD-NI | CTGACCCCAGAGCAGGTCGTGGCGATCGCAAGCCACGACGGAG GAAAGCAAGCCTTGGAAACAGTACAGAGGCTGTTGCCTGTGCTTT GTCAGGCACACGGCCTCACTCCGGAACAAGTGGTCGCAATCGCCT CCAACATTGGCGGGAAACAGGCACTCGAGACTGTCCAGCGCCTG CTTCCCGTGCTGTGCCAAGCGCACGGT | SEQ ID NO: 13 |
| HD-NG | CTGACCCCAGAGCAGGTCGTGGCGATCGCAAGCCACGACGGAG GAAAGCAAGCCTTGGAAACAGTACAGAGGCTGTTGCCTGTGCTTT GTCAGGCACACGGCCTCACTCCGGAACAAGTGGTCGCCATTGCCT CGAATGGAGGGGGCAAACAGGCGTTGGAAACCGTACAACGATT GCTGCCGGTGCTGTGCCAAGCGCACGGT | SEQ ID NO: 14 |
| HD-HD | CTGACCCCAGAGCAGGTCGTGGCGATCGCAAGCCACGACGGAG GAAAGCAAGCCTTGGAAACAGTACAGAGGCTGTTGCCTGTGCTTT | SEQ ID NO: 15 |

TABLE 1 -continued

| Name | Sequence | SEQ ID |
|---|---|---|
| | GTCAGGCACACGGCCTCACTCCGGAACAAGTGGTCGCGATCGCA<br>AGCCACGACGGAGGAAAGCAAGCCTTGGAAACAGTACAGAGGC<br>TGTTGCCTGTGCTGTGCCAAGCGCACGGT | |
| HD-NN | CTCACCCCAGAGCAGGTCGTGGCGATCGCAAGCCACGACGGAGG<br>AAAGCAAGCCTTGGAAACAGTACAGAGGCTGTTGCCTGTGCTTTG<br>TCAGGCACACGGCCTCACTCCGGAACAAGTGGTCGCAATCGCGA<br>GCAATAACGGCGGAAAACAGGCTTTGGAAACGGTGCAGAGGCT<br>CCTTCCAGTGCTGTGCCAAGCGCACGGA | SEQ ID NO: 16 |
| NN-NI | CTGACCCCAGAGCAGGTCGTGGCAATCGCGAGCAATAACGGCGG<br>AAAACAGGCTTTGGAAACGGTGCAGAGGCTCCTTCCAGTGCTTTG<br>TCAGGCACACGGCCTCACTCCGGAACAAGTGGTCGCAATCGCCTC<br>CAACATTGGCGGGAAACAGGCACTCGAGACTGTCCAGCGCCTGC<br>TTCCCGTGCTGTGCCAAGCGCACGGT | SEQ ID NO: 17 |
| NN-NG | CTGACCCCAGAGCAGGTCGTGGCAATCGCGAGCAATAACGGCGG<br>AAAACAGGCTTTGGAAACGGTGCAGAGGCTCCTTCCAGTGCTTTG<br>TCAGGCACACGGCCTCACTCCGGAACAAGTGGTCGCCATTGCCTC<br>GAATGGAGGGGGCAAACAGGCGTTGGAAACCGTACAACGATTG<br>CTGCCGGTGCTGTGCCAAGCGCACGGT | SEQ ID NO: 18 |
| NN-HD | CTGACCCCAGAGCAGGTCGTGGCAATCGCGAGCAATAACGGCGG<br>AAAACAGGCTTTGGAAACGGTGCAGAGGCTCCTTCCAGTGCTTTG<br>TCAGGCACACGGCCTCACTCCGGAACAAGTGGTCGCGATCGCAA<br>GCCACGACGGAGGAAAGCAAGCCTTGGAAACAGTACAGAGGCT<br>GTTGCCTGTGCTGTGCCAAGCGCACGGT | SEQ ID NO: 19 |
| NN-NN | CTGACCCCAGAGCAGGTCGTGGCAATCGCGAGCAATAACGGCGG<br>AAAACAGGCTTTGGAAACGGTGCAGAGGCTCCTTCCAGTGCTTTG<br>TCAGGCACACGGCCTCACTCCGGAACAAGTGGTCGCAATCGCGA<br>GCAATAACGGCGGAAAACAGGCTTTGGAAACGGTGCAGAGGCT<br>CCTTCCAGTGCTGTGCCAAGCGCACGGT | SEQ ID NO: 20 |

EXAMPLES

A DNA library including 172 DNA segments was established by modifying the TALE repeat modules described above. PCR amplification was applied to add restriction enzyme cutting sites and adaptors. For dimers, PCR was performed using T-vectors containing 16 dimers and primer pairs including F1 and R1, F2 and R2, F3 and R3, F4 and R4, F5 and R5, F6 and R6, F7 and R7, F8 and R8, as well as F9 and R9. There were 144 (i.e., 16×9) PCR products. For monomers, PCR was performed using T-vectors containing 4 monomers and primer pairs including F1 and R1, F2 and R2, F3 and R3, F4 and R4, F5 and R5, F6 and R6, as well as F7 and R7. There were 28 (i.e., 4×7) PCR products. Thus, the DNA library includes 172 PCT products (i.e., 144 plus 28). Exemplary sequences of primer pairs F1 and R1, F2 and R2, F3 and R3, F4 and R4, F5 and R5, F6 and R6, F7 and R7, F8 and R8, as well as F9 and R9 may be listed in Table 2, and lower case letter indicates BsaI cutting sites.

TABLE 2

| Name | Sequence | SEQ ID |
|---|---|---|
| TALE-F1 | AATGGACGACCCGGCTTGATAggtctcc*TGAC*CCCAGAGCAGGTCGTGG | SEQ ID NO: 21 |
| TALE-R1 | CATCACAGGTAGCTCGCTGGAggtctcT*TAAA*CCGTGCGCTTGGCAC | SEQ ID NO: 22 |
| TALE-F2 | ATCGATCGATCGCGATCGATCggtctcG*TTTA*ACCCCAGAGCAGGTCGTG | SEQ ID NO: 23 |
| TALE-R2 | GCAGCCACGGCTAGCTTAAGCggtctcT*GAGG*CCGTGCGCTTGCAC | SEQ ID NO: 24 |
| TALE-F3 | ATCGATCGATCGCGATCGATCggtctcG*CCTC*ACCCCAGAGCAGGTCGTG | SEQ ID NO: 25 |
| TALE-R3 | GAACCGCCGTCTTACGTAGAGggtctcT*TAAT*CCGTGCGCTTGCAC | SEQ ID NO: 26 |
| TALE-F4 | TTTAGCCCGTACCGTAGCCTAggtctcG*ATTA*ACCCCAGAGCAGGTCGTG | SEQ ID NO: 27 |
| TALE-R4 | TTGCACCGGTATCGTCGAGGCggtctcT*AAGT*CCGTGCGCTTGCAC | SEQ ID NO: 28 |

TABLE 2 -continued

| Name | Sequence | SEQ ID |
|---|---|---|
| TALE-F5 | AAGCATGGATCGCAAGGGTTGggtctcG*ACTT*ACCCCAGAGC AGGTCGTG | SEQ ID NO: 29 |
| TALE-R5 | GGGTTGCGCTCGCAATTACCGggtctcT*AAGG*CCGTGCGCTTG GCAC | SEQ ID NO: 30 |
| TALE-F6 | CGAAATCCGACCGGATGCCTAggtctcG*CCTT*ACCCCAGAGCA GGTCGTG | SEQ ID NO: 31 |
| TALE-R6 | GCCATCGCGTCGCACGAAGCTggtctcT*TAGT*CCGTGCGCTTG GCAC | SEQ ID NO: 32 |
| TALE-F7 | ATAGCTGGTAGGGCTACGGGCggtctcG*ACTA*ACCCCAGAGC AGGTCGTG | SEQ ID NO: 33 |
| TALE-R7 | GAACGACCCCTGACAGTCGTTggtctcT*GAGC*CCGTGCGCTTG GCAC | SEQ ID NO: 34 |
| TALE-F8 | CGATATCGATCGCCTTACGCggtctcG*GCTC*ACCCCAGAGCAG GTCGTG | SEQ ID NO: 35 |
| TALE-R8 | CGCCACATATATAGCGCGTCCggtctcT*TAGC*CCGTGCGCTIGG CAC | SEQ ID NO: 36 |
| TALE-F9 | GTGTGACGGCTAGCCTAGTAggtctcG*GCTA*ACCCCAGAGCA GGTCGTG | SEQ ID NO: 37 |
| TALE-R9 | GCTTGCGGATCGATAGCATGGggtctcT*GAGT*CCGTGCGCTTG GCAC | SEQ ID NO: 38 |

Regarding the PCR, approximately 1 μl Plasmid was mixed with a solution containing 0.2 μl Primers (0.1 μl for each of the primer pair), 1.5 μl Buffer, 0.8 μl dNTP, 0.35 μl MgSO4, 11.48 μl ddH2O, and 1 Unit DNA Polymerase. The following PCR reaction was used: 36 cycles 95° C. for 2 min, 95° C. for 15 sec, 55.8° C. for 30 sec, 68° C. for 30 sec, 68° C. for 2 sec, and followed by 68° C. for 1 min.

All 18 primers contain a BsaI cutting site: GGTCTCN'NNNN (SEQ ID NO: 49), wherein N represents a nucleotide. BsaI belongs to type II restriction endonuclease, and one cutting site can generate various overhangs. Using type II restriction endonuclease, 24 fusion sites were generated with respect to 4 codons for Gly and 6 codons for Leu. In addition, 10 of those 24 were selected for primer designs. Except for F1 and R9, Fk can specifically ligate to Rk-1, but not other primers, wherein k is an integer between 3 and 9.

Figure 1B:
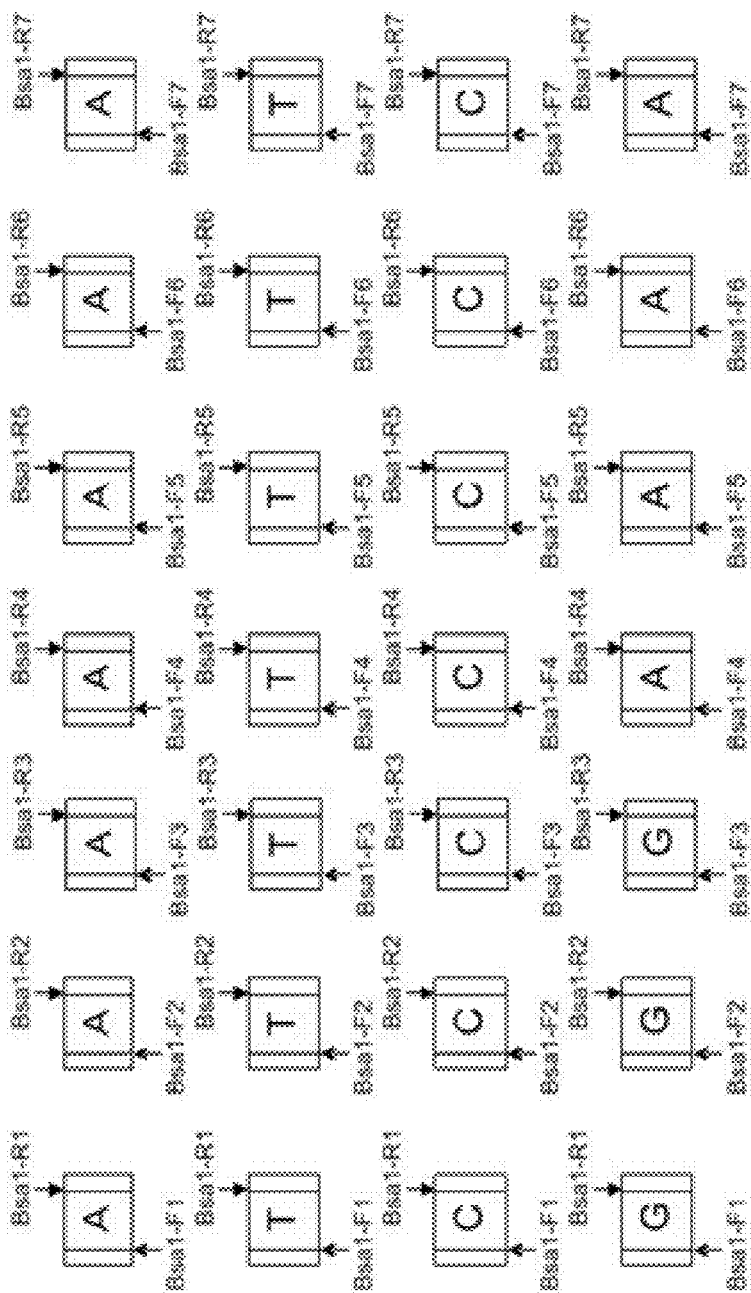
FIG. 1B is a diagram showing an exemplary DNA library including monomer repeat modules.

The 172 PCR products were purified by gel extraction, ligated and inserted into pMD18-T plasmids. The following ligation of 20 original modules into pMD18-T (from Takara) was used. First, 2.7 μl PCR products was mixed with a solution containing 3 μl solution 1 and 0.3 μl pMD18-T. Then, the mixture was incubated at 16° C. for 2 hours, transformed into DH5a, and stroke onto LB plates containing kanamycin. Colonies were selected, and plasmids were isolated. The PCR products were verified by PCR and sequencing. Finally, a plasmid library containing 172 plasmids were established, as illustrated in FIG. 1.

A PCR product library was generated using assem-F and assem-R as primers (e.g., sequences in Table 3) and plasmids of the 172 plasmid library as PCR templates. The binding sites of primers are 400 by upstream and downstream of polynucleotides encoding individual TALE repeat modules. In addition, the PCR products for dimers are about 1050 by and for monomers are about 950 bp.

TABLE 3

| Name | Sequence | SEQ ID |
|---|---|---|
| assem-F | TGTTGTGTGGAATTGTGAGCGGATAAC | SEQ ID NO: 39 |
| assem-R | TGCAAGGCGATTAAGTTGGGTAACG | SEQ ID NO: 40 |

For PCR amplification (50 μl), 0.5 μl DNA template (about 50 ng) was mixed with a solution containing 0.3 μl (50 μM) for each primer, 0.25 μl pfx polymerase (Invitrogen), 5 μl 10× buffer, 2.5 μl dNTP (2.5 μM), 1 ul MgSO4, 40.15 μl ddH2O. The following PCR amplification program was used: 36 cycles 95° C. for 2 min, 95° C. for 15 sec, 68° C. for 30 sec, 68° C. for 50 sec, and followed by 68° C. for 5 min.

Figure 2:
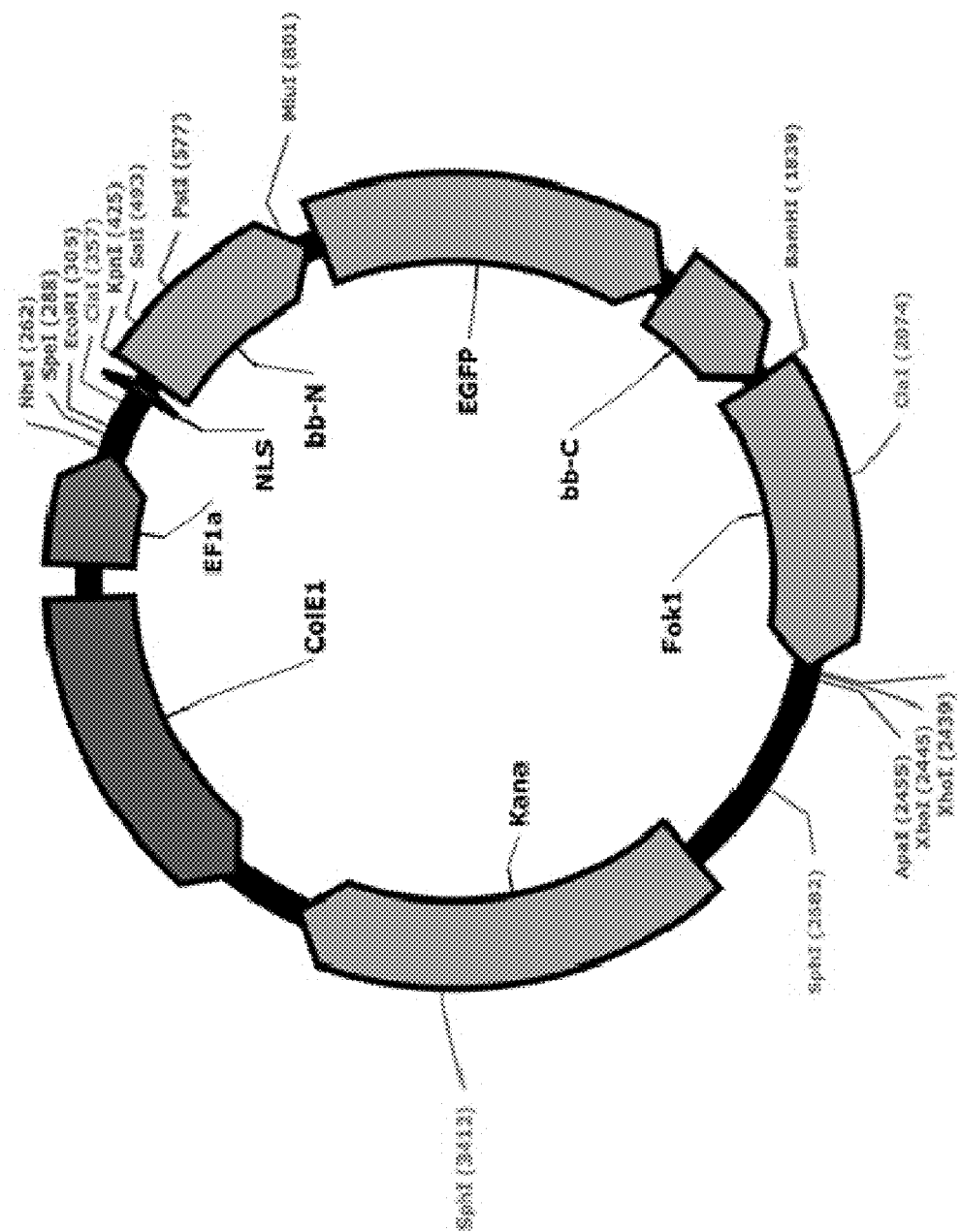
FIG. 2 is a diagram showing an exemplary TALEN backbone plasmid.
Figure 3:
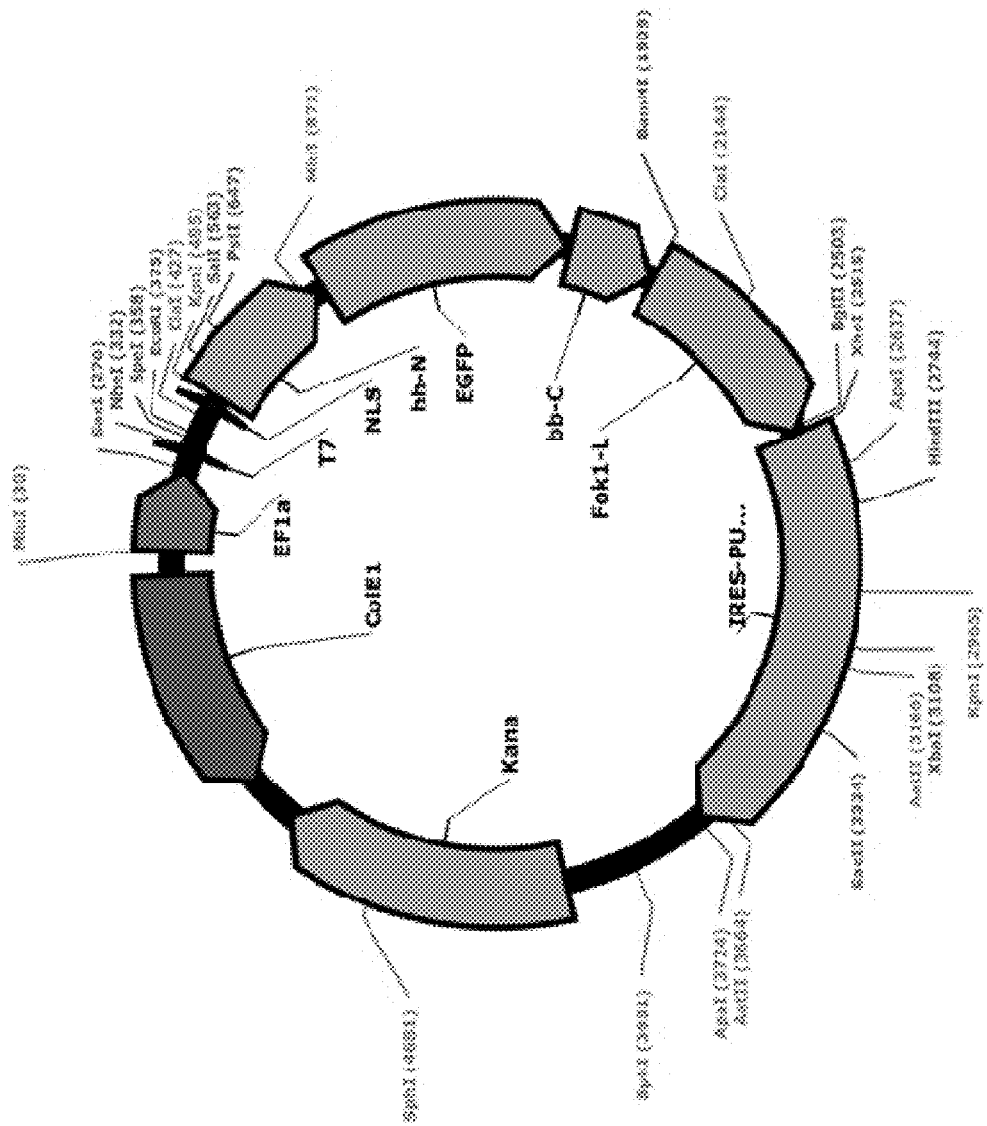
FIG. 3 is a diagram showing another exemplary TALEN backbone plasmid.

The PCR products were purified using DNA purification kits (Taingen), and measured concentrations by agar gel electrophoresis. Enzyme digestion sites of two TALEN plasmids: pEF1a-NLS-TALE backbone-Fok1(R)-pA and pEF1a-NLS-TALE backbone-Fok1(L)-IRES-PURO-pA, were illustrated in FIGS. 2 and 3 respectively. The sequences are shown as SEQ ID NO: 41 and SEQ ID NO: 42. Sequences of N-terminal and C-terminal of transcription activator-like effectors are shown as SEQ ID NO: 43 and SEQ ID NO: 44. Before ligation, BsaI was added to digest TALEN vectors to obtain overhangs for repeats modules. Digested TALEN vectors were purified by gel extraction, and concentrations were determined by gel electrophoresis.

With respect to TALEN ligation, except? for F1 and R9 (F1 ligates to left end of TALEN vector, R9 ligates to right end of backbone vector), Fk can ligate to Rk-1 at overhangs, but not to others. After ligations, BsaI is not able to break modules and backbone vectors.

Figure 4:
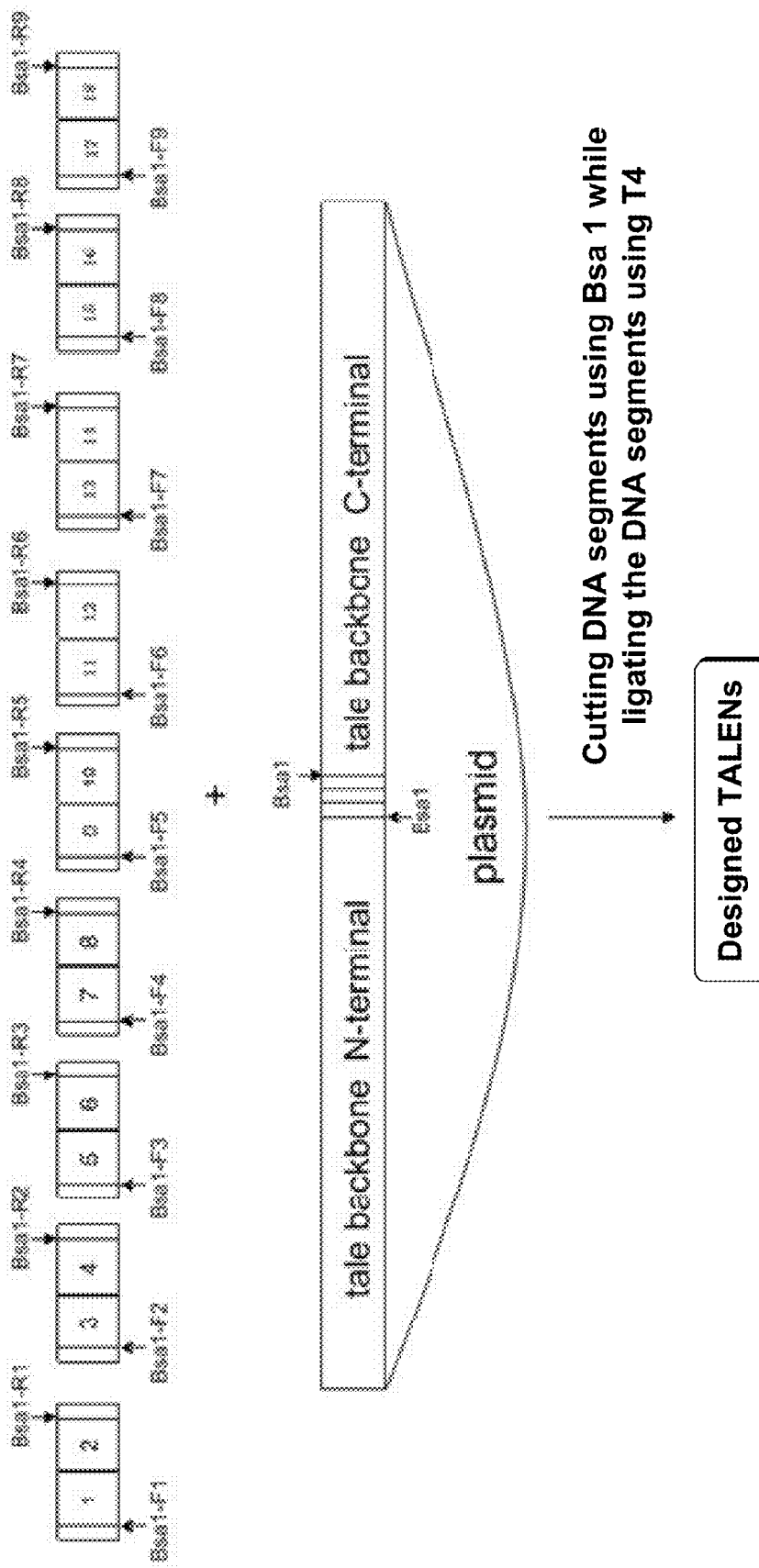
FIG. 4 is an exemplary process showing 19 modules ligation.

FIG. 4 illustrates a process for assembling a TALEN containing 19 repeat segments. As illustrated, the last half DNA segment encoding a module recognizing T is in the backbone vector already; thus the ligation of 18 modules is enough. 9

DNA segments may be selected based on target sequences, and mixed with a solution containing TALEN backbone vector, BsaI, and T4 ligase to digest and ligate in the same reactor or system.

The following assembly system was used: 150 ng vector, 50 ng each DNA segment, 1 μl BsaI (NEB), 1 μl T4 ligase (Fermentas), 2 μl T4 Buffer (NEB), and double-distilled water (ddH₂O) to make to final 20 μl. The following ligation program was used: 15 cycles 37° C. for 5 min, 16° C. for 10 min, and followed by 80° C. for 10 min.

If occasional incomplete ligation happens (e.g., only 1 to 8 modules are ligated), this incomplete ligation may slow down the ligation efficiency by recombination. Thus, before transformation, a Plasmid-Safe™ ATP-Dependent DNase (Epicentre, cat no: E3105K) may be used to digest the linear plasmids. To remove the linear plasmids, 1 μl plasmid-safe DNases and 0.5 μl ATP were added into a 20 μl ligation system for an additional incubation at 37° C. for 1 hour. 10 μl of ligation products were taken to transform Trans-T1 competent cells. Colonies were selected to obtain isolated vectors. Restriction analysis was performed by using BamH1/Pst1. The expected size of smaller fragment is the length of ligated size plus 550 bp. The final precuts were sent for sequencing. Exemplary sequencing primers are listed in table 4.

TABLE 4

| Name | Sequence | SEQ ID |
|---|---|---|
| Sequence-F | CTCCCCTCAGCTGGACAC | SEQ ID NO: 45 |
| Sequence-R | AGCTGGGCCACGATTGAC | SEQ ID NO: 46 |

Embodiments of this disclosure allow obtaining sequence-confirmed TALEN vectors within 3 days. For example, the ligation (4.5 hours), plasmid-safe DNase digestion (1 hour), and transformation (1 hour) may be performed in the first day. Colonies selection and bacterial inculcation may be performed in day 2. Finally, the sequence analysis results may be received in day 3. If the target sequence is 12-18 but not 19, the modules located in the front part can be changed from dimers into monomers, and thus the change of dimer to monomer can reduce a module. Exemplary options for different monomers or dimers specific to the targeting nucleotide(s) are shown in picture 6.

In some embodiments, polynucleotides encoding TALENs for targeting certain sequences may be assembled in a single reaction. Examples of the sequences may be found in table 5.

TABLE 5

| Name | Sequence | SEQ ID |
|---|---|---|
| Sequence 1 | CGCGCGCGCGCGCGCGCGT | SEQ ID NO: 47 |
| Sequence 2 | CCCACTCCCCATCCAGT | SEQ ID NO: 48 |

In these instances, DNA segments encoding repeat modules were selected from the PCR library. For example, for sequence 1, DNA segments corresponding to CG-1, CG-2, CG-3, CG-4, CG-5, CG-6, CG-7, CG-8, and CG-9 were chosen, and TALEN vectors containing pEF1a-NLS-TALE backbone-Fok1(R)-pA were used. For sequence 2, DNA segments corresponding to C-1, A-2, C-3, TC-4, CC-5, CA-6, TC-7, CA-8, and GT-9 were chosen, and TALEN vectors containing pEF1a-NLS-TALE backbone-Fok1 (L)-IRES-PURO-pA were used. The following assembly system was used: 150 ng vector, 50 ng each modules, 1 μl BsaI (NEB), 1 μl T4 Ligase (fermentas), 2 μl T4 Buffer (NEB), and H₂O to make the system solution to final 20 μl. The following Ligation program was used for 15 cycles: 37° C. for 5 min, and 16° C. for 10 min, and followed by 80° C. for 10 min.

Figure 7:
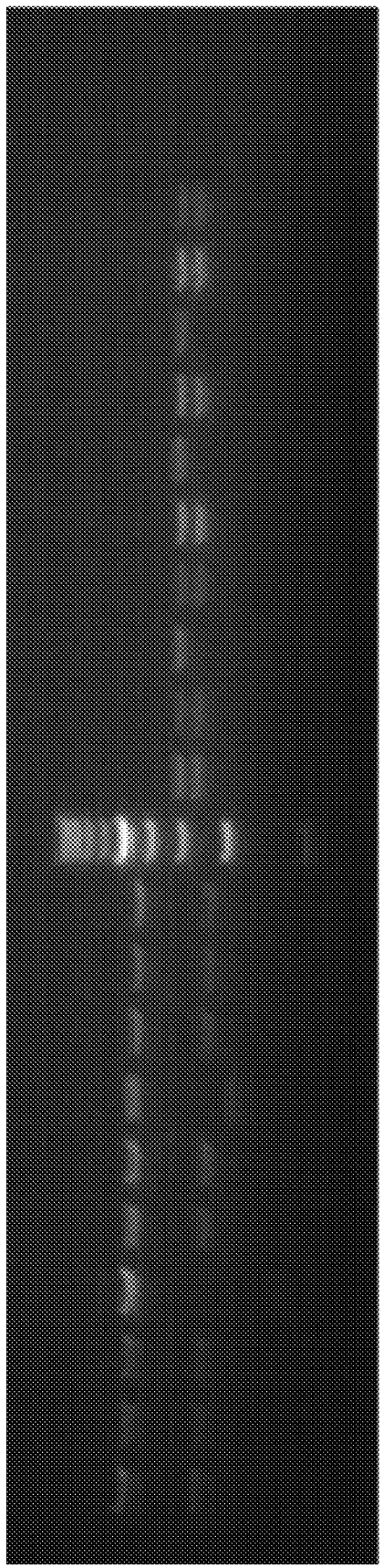
FIG. 7 is a photograph of an agarose gel electrophoresis showing confirmation of assembly clones by restriction digestion analysis.

The ligation products were purified using plasmid-safe DNases for 1 hour. The products (plasmids) were then transformed into Trans-T1 chemically competent cells. The plasmids were isolated and analyzed by BamH1\EcoR1 restriction digestion and gel electrophoresis. FIG. 7 is a photograph of an agarose gel electrophoresis showing confirmation of assembly clones by restriction digestion analysis. As illustrated, enzyme digestion bands include: 1 kb DNA marker in the middle lane, ligation I indicating 3.1 kb and 2.2 kb on the right of the DNA marker, and ligation II indicating 4.2 kb and 3.7 kb on the left of the DNA marker. Cloning efficiency for assembling TALENs containing recognition domains to identify Sequence 1 and Sequence 2 in a single reaction is 70% and 80% respectively.

What is claimed is:

1. A method for assembling a polynucleotide encoding a transcription activator-like effector (TALE) polypeptide, the method comprising:
generating multiple Deoxyribonucleic acid (DNA) segments, an individual DNA segment of the multiple DNA segments corresponding to a repeat sequence of the TALE polypeptide, the repeat sequence identifying a single nucleotide of a particular target polynucleotide or two contiguous nucleotides of the particular target polynucleotide;
mixing the multiple DNA segments with restriction enzymes, DNA ligases, and a TALE backbone vector to generate the polynucleotide encoding the TALE polypeptide, a number of multiple DNA segments being greater than 14; and
purifying the polynucleotide using a plasmid-safe Deoxyribonuclease (DNase).

2. The method of claim 1, wherein the multiple DNA segments are polymerase chain reaction (PCR) amplification products or a plasmid.

3. The method of claim 1, wherein the number of multiple DNA segments is greater than 18.

4. The method of claim 1, wherein the mixing the multiple DNA segments with the restriction enzymes, the DNA ligases, and the TALE backbone vector comprises mixing the multiple DNA segments with the restriction enzymes, the DNA ligases, and the TALE backbone vector in a reaction system.

5. The method of claim 1, wherein the mixing the multiple DNA segments with the restriction enzymes, the DNA ligases, and the TALE backbone vector comprises mixing the multiple DNA segments with the restriction enzymes, the DNA ligases, and the TALE backbone vectors under a condition including multiple temperature cyclings.

6. The method of claim 5, wherein the multiple temperature cyclings is followed by inactivation of the restriction enzymes.

7. The method of claim 1, wherein the mixing the multiple DNA segments with the restriction enzymes, the DNA ligases, and the TALE backbone vector comprises mixing the multiple DNA segments with the restriction enzymes that belongs to a type of type II restriction enzymes, the DNA ligases, and the TALE backbone vectors without other types of the type II restriction enzymes.

8. The method of claim 1, wherein the individual DNA segment of the multiple DNA segments has two cleavage sites that are generated using type II restriction enzymes, and wherein the restriction enzymes are the type II restriction enzymes.

9. A kit for generating polynucleotides encoding a transcription activator-like effector (TALE) polypeptide, the kit comprising:
multiple sets of dimer DNA segments, an individual set of dimer DNA segments including multiple dimer DNA segments, an individual dimer DNA segment encoding two recognition domains of a designed TALE that identify two contiguous nucleotides of a particular target polynucleotide;
multiple sets of monomer DNA segments, an individual set of monomer DNA segments including multiple monomer DNA modules, an individual monomer DNA module encoding a recognition domain of the designed TALE that identifies a single nucleotide of the particular target polynucleotide, wherein the individual dimer DNA segments and the individual monomer DNA segments including a first overhang and a second overhang that are generated using a type II restriction endonuclease;
restriction enzymes;
DNA ligases; and
TALE backbone vectors.

10. The Kit of claim 9, wherein a sequence of a first overhang of a dimer DNA segment of multiple dimer DNA segments is complementary to a sequence of a second overhang of a particular dimer NDA segment that is ligated to the dimer DNA segment.

11. The Kit of claim 9, wherein a sequence of a first overhang of a monomer DNA segment of multiple monomer DNA segments is complementary to a sequence of a second overhang of a particular monomer DNA segment that is ligated to the monomer DNA segment.

12. The Kit of claim 9, wherein the type II restriction endonuclease is Bsa I.

13. The Kit of claim 9, wherein a number of the multiple sets of dimer DNA segments is from 8 to 10, and a number of the multiple sets of monomer DNA segments is from 6 to 8.

14. The Kit of claim 9, wherein an individual set of dimer DNA segments includes 15 to 17 dimer DNA segments, and an individual set of monomer DNA segments include 3 to 5 monomer DNA segments.

15. The Kit of claim 9, wherein the multiple dimer DNA segments and the multiple monomer DNA segments include an overlap extension polymerase chain reaction (PCR) product or a plasmid.

16. The Kit of claim 9, wherein the multiple dimer DNA segments and the multiple monomer DNA segments include pMD18-T.

* * * * *

SEQUENCE LISTING

```
<160> NUMBER OF SEQ ID NOS: 48

<210> SEQ ID NO 1
<211> LENGTH: 102
<212> TYPE: DNA
<213> ORGANISM: Artificial Sequence
<220> FEATURE:
<223> OTHER INFORMATION: NI

<400> SEQUENCE: 1 ctgacccag agcaggtcgt ggcaatcgcc tccaacattg gcgggaaaca ggcactcgag      60
actgtccagc gcctgcttcc cgtgctgtgc caagcgcacg ga                      102

<210> SEQ ID NO 2
<211> LENGTH: 102
<212> TYPE: DNA
<213> ORGANISM: Artificial Sequence
<220> FEATURE:
<223> OTHER INFORMATION: NG

<400> SEQUENCE: 2
```
ctgaccccag agcaggtcgt ggccattgcc tcgaatggag ggggcaaaca ggcgttggaa      60
accgtacaac gattgctgcc ggtgctgtgc caagcgcacg gc                        102

<210> SEQ ID NO 3
<211> LENGTH: 102
<212> TYPE: DNA
<213> ORGANISM: Artificial Sequence
<220> FEATURE:
<223> OTHER INFORMATION: HD

<400> SEQUENCE: 3
ttgaccccag agcaggtcgt ggcgatcgca agccacgacg gaggaaagca agccttggaa      60
acagtacaga ggctgttgcc tgtgctgtgc caagcgcacg gg                        102

<210> SEQ ID NO 4
<211> LENGTH: 102
<212> TYPE: DNA
<213> ORGANISM: Artificial Sequence
<220> FEATURE:
<223> OTHER INFORMATION: NN

<400> SEQUENCE: 4
ctgaccccag agcaggtcgt ggcaatcgcg agcaataacg gcggaaaaca ggctttggaa      60
acggtgcaga ggctccttcc agtgctgtgc caagcgcacg gt                        102

<210> SEQ ID NO 5
<211> LENGTH: 204
<212> TYPE: DNA
<213> ORGANISM: Artificial Sequence
<220> FEATURE:
<223> OTHER INFORMATION: NI-NI

<400> SEQUENCE: 5
ctgaccccag agcaggtcgt ggcaatcgcc tccaacattg gcgggaaaca ggcactcgag      60
actgtccagc gcctgcttcc cgtgctttgt caggcacacg gcctcactcc ggaacaagtg     120
gtcgcaatcg cctccaacat tggcgggaaa caggcactcg agactgtcca gcgcctgctt     180
cccgtgctgt gccaagcgca cggt                                            204

<210> SEQ ID NO 6
<211> LENGTH: 204
<212> TYPE: DNA
<213> ORGANISM: Artificial Sequence
<220> FEATURE:
<223> OTHER INFORMATION: NI-NG

<400> SEQUENCE: 6
ctgaccccag agcaggtcgt ggcaatcgcc tccaacattg gcgggaaaca ggcactcgag      60
actgtccagc gcctgcttcc cgtgctttgt caggcacacg gcctcactcc ggaacaagtg     120
gtcgccattg cctcgaatgg aggggcaaa caggcgttgg aaaccgtaca acgattgctg     180
ccggtgctgt gccaagcgca cggt                                            204

<210> SEQ ID NO 7
<211> LENGTH: 204
<212> TYPE: DNA
<213> ORGANISM: Artificial Sequence
<220> FEATURE:
<223> OTHER INFORMATION: NI-HD

<400> SEQUENCE: 7

```
ctgaccccag agcaggtcgt ggcaatcgcc tccaacattg gcgggaaaca ggcactcgag      60
actgtccagc gcctgcttcc cgtgctttgt caggcacacg gcctcactcc ggaacaagtg     120
gtcgcgatcg caagccacga cggaggaaag caagccttgg aaacagtaca gaggctgttg     180
cctgtgctgt gccaagcgca cggt                                            204

<210> SEQ ID NO 8
<211> LENGTH: 204
<212> TYPE: DNA
<213> ORGANISM: Artificial Sequence
<220> FEATURE:
<223> OTHER INFORMATION: NI-NN

<400> SEQUENCE: 8
ctgaccccag agcaggtcgt ggcaatcgcc tccaacattg gcgggaaaca ggcactcgag      60
actgtccagc gcctgcttcc cgtgctttgt caggcacacg gcctcactcc ggaacaagtg     120
gtcgcaatcg cgagcaataa cggcggaaaa caggctttgg aaacggtgca gaggctcctt     180
ccagtgctgt gccaagcgca cggt                                            204

<210> SEQ ID NO 9
<211> LENGTH: 204
<212> TYPE: DNA
<213> ORGANISM: Artificial Sequence
<220> FEATURE:
<223> OTHER INFORMATION: NG-NI

<400> SEQUENCE: 9
ctgaccccag agcaggtcgt ggccattgcc tcgaatggag ggggcaaaca ggcgttggaa      60
accgtacaac gattgctgcc ggtgctttgt caggcacacg gcctcactcc ggaacaagtg     120
gtcgcaatcg cctccaacat tggcgggaaa caggcactcg agactgtcca gcgcctgctt     180
cccgtgctgt gccaagcgca cggt                                            204

<210> SEQ ID NO 10
<211> LENGTH: 204
<212> TYPE: DNA
<213> ORGANISM: Artificial Sequence
<220> FEATURE:
<223> OTHER INFORMATION: NG-NG

<400> SEQUENCE: 10
ctgaccccag agcaggtcgt ggccattgcc tcgaatggag ggggcaaaca ggcgttggaa      60
accgtacaac gattgctgcc ggtgctttgt caggcacacg gcctcactcc ggaacaagtg     120
gtcgccattg cctcgaatgg aggggggcaaa caggcgttgg aaaccgtaca acgattgctg    180
ccggtgctgt gccaagcgca cggt                                            204

<210> SEQ ID NO 11
<211> LENGTH: 204
<212> TYPE: DNA
<213> ORGANISM: Artificial Sequence
<220> FEATURE:
<223> OTHER INFORMATION: NG-HD

<400> SEQUENCE: 11
ctgaccccag agcaggtcgt ggccattgcc tcgaatggag ggggcaaaca ggcgttggaa      60
accgtacaac gattgctgcc ggtgctttgt caggcacacg gcctcactcc ggaacaagtg     120
gtcgcgatcg caagccacga cggaggaaag caagccttgg aaacagtaca gaggctgttg     180
cctgtgctgt gccaagcgca cggt                                            204
```

-continued

<210> SEQ ID NO 12
<211> LENGTH: 204
<212> TYPE: DNA
<213> ORGANISM: Artificial Sequence
<220> FEATURE:
<223> OTHER INFORMATION: NG-NN

<400> SEQUENCE: 12
ctgaccccag agcaggtcgt ggccattgcc tcgaatggag ggggcaaaca ggcgttggaa     60
accgtacaac gattgctgcc ggtgctttgt caggcacacg gcctcactcc ggaacaagtg    120
gtcgcaatcg cgagcaataa cggcggaaaa caggctttgg aaacggtgca gaggctcctt    180
ccagtgctgt gccaagcgca cggt                                          204

<210> SEQ ID NO 13
<211> LENGTH: 204
<212> TYPE: DNA
<213> ORGANISM: Artificial Sequence
<220> FEATURE:
<223> OTHER INFORMATION: HD-NI

<400> SEQUENCE: 13
ctgaccccag agcaggtcgt ggcgatcgca agccacgacg aggaaagca agccttggaa      60 acagtacaga ggctgttgcc tgtgctttgt caggcacacg gcctcactcc ggaacaagtg    120
gtcgcaatcg cctccaacat tggcgggaaa caggcactcg agactgtcca gcgcctgctt   180
cccgtgctgt gccaagcgca cggt                                          204

<210> SEQ ID NO 14
<211> LENGTH: 204
<212> TYPE: DNA
<213> ORGANISM: Artificial Sequence
<220> FEATURE:
<223> OTHER INFORMATION: HD-NG

<400> SEQUENCE: 14
ctgaccccag agcaggtcgt ggcgatcgca agccacgacg aggaaagca agccttggaa      60 acagtacaga ggctgttgcc tgtgctttgt caggcacacg gcctcactcc ggaacaagtg    120
gtcgccattg cctcgaatgg agggggcaaa caggcgttgg aaaccgtaca acgattgctg   180
ccggtgctgt gccaagcgca cggt                                          204

<210> SEQ ID NO 15
<211> LENGTH: 204
<212> TYPE: DNA
<213> ORGANISM: Artificial Sequence
<220> FEATURE:
<223> OTHER INFORMATION: HD-HD

<400> SEQUENCE: 15
ctgaccccag agcaggtcgt ggcgatcgca agccacgacg aggaaagca agccttggaa      60 acagtacaga ggctgttgcc tgtgctttgt caggcacacg gcctcactcc ggaacaagtg    120
gtcgcgatcg caagccacga cggaggaaag caagccttgg aaacagtaca gaggctgttg   180
cctgtgctgt gccaagcgca cggt                                          204

<210> SEQ ID NO 16
<211> LENGTH: 204
<212> TYPE: DNA
<213> ORGANISM: Artificial Sequence
<220> FEATURE:

<223> OTHER INFORMATION: HD-NN

<400> SEQUENCE: 16
ctcaccccag agcaggtcgt ggcgatcgca agccacgacg aggaaagca agccttggaa      60 acagtacaga ggctgttgcc tgtgctttgt caggcacacg gcctcactcc ggaacaagtg    120
gtcgcaatcg cgagcaataa cggcggaaaa caggctttgg aaacggtgca gaggctcctt    180
ccagtgctgt gccaagcgca cgga                                            204

<210> SEQ ID NO 17
<211> LENGTH: 204
<212> TYPE: DNA
<213> ORGANISM: Artificial Sequence
<220> FEATURE:
<223> OTHER INFORMATION: NN-NI

<400> SEQUENCE: 17
ctgaccccag agcaggtcgt ggcaatcgcg agcaataacg gcggaaaaca ggctttggaa     60
acggtgcaga ggctccttcc agtgctttgt caggcacacg gcctcactcc ggaacaagtg   120
gtcgcaatcg cctccaacat tggcgggaaa caggcactcg agactgtcca gcgcctgctt   180
cccgtgctgt gccaagcgca cggt                                           204

<210> SEQ ID NO 18
<211> LENGTH: 204
<212> TYPE: DNA
<213> ORGANISM: Artificial Sequence
<220> FEATURE:
<223> OTHER INFORMATION: NN-NG

<400> SEQUENCE: 18
ctgaccccag agcaggtcgt ggcaatcgcg agcaataacg gcggaaaaca ggctttggaa     60
acggtgcaga ggctccttcc agtgctttgt caggcacacg gcctcactcc ggaacaagtg   120
gtcgccattg cctcgaatgg aggggggcaaa caggcgttgg aaaccgtaca acgattgctg  180
ccggtgctgt gccaagcgca cggt                                           204

<210> SEQ ID NO 19
<211> LENGTH: 204
<212> TYPE: DNA
<213> ORGANISM: Artificial Sequence
<220> FEATURE:
<223> OTHER INFORMATION: NN-HD

<400> SEQUENCE: 19
ctgaccccag agcaggtcgt ggcaatcgcg agcaataacg gcggaaaaca ggctttggaa     60
acggtgcaga ggctccttcc agtgctttgt caggcacacg gcctcactcc ggaacaagtg   120
gtcgcgatcg caagccacga cggaggaaag caagccttgg aaacagtaca gaggctgttg   180
cctgtgctgt gccaagcgca cggt                                           204

<210> SEQ ID NO 20
<211> LENGTH: 204
<212> TYPE: DNA
<213> ORGANISM: Artificial Sequence
<220> FEATURE:
<223> OTHER INFORMATION: NN-NN

<400> SEQUENCE: 20
ctgaccccag agcaggtcgt ggcaatcgcg agcaataacg gcggaaaaca ggctttggaa     60
acggtgcaga ggctccttcc agtgctttgt caggcacacg gcctcactcc ggaacaagtg   120

```
gtcgcaatcg cgagcaataa cggcggaaaa caggctttgg aaacggtgca gaggctcctt      180
ccagtgctgt gccaagcgca cggt                                             204

<210> SEQ ID NO 21
<211> LENGTH: 49
<212> TYPE: DNA
<213> ORGANISM: Artificial Sequence
<220> FEATURE:
<223> OTHER INFORMATION: TALE-F1

<400> SEQUENCE: 21
aatggacgac ccggcttgat aggtctcctg accccagagc aggtcgtgg                   49

<210> SEQ ID NO 22
<211> LENGTH: 47
<212> TYPE: DNA
<213> ORGANISM: Artificial Sequence
<220> FEATURE:
<223> OTHER INFORMATION: TALE-R1

<400> SEQUENCE: 22
catcacaggt agctcgctgg aggtctctta aaccgtgcgc ttggcac                     47

<210> SEQ ID NO 23
<211> LENGTH: 50
<212> TYPE: DNA
<213> ORGANISM: Artificial Sequence
<220> FEATURE:
<223> OTHER INFORMATION: TALE-F2

<400> SEQUENCE: 23
atcgatcgat cgcgatcgat cggtctcgtt taaccccaga gcaggtcgtg                  50

<210> SEQ ID NO 24
<211> LENGTH: 47
<212> TYPE: DNA
<213> ORGANISM: Artificial Sequence
<220> FEATURE:
<223> OTHER INFORMATION: TALE-R2

<400> SEQUENCE: 24
gcagccacgg ctagcttaag cggtctctga ggccgtgcgc ttggcac                     47

<210> SEQ ID NO 25
<211> LENGTH: 50
<212> TYPE: DNA
<213> ORGANISM: Artificial Sequence
<220> FEATURE:
<223> OTHER INFORMATION: TALE-F3

<400> SEQUENCE: 25
atcgatcgat cgcgatcgat cggtctcgcc tcaccccaga gcaggtcgtg                  50

<210> SEQ ID NO 26
<211> LENGTH: 47
<212> TYPE: DNA
<213> ORGANISM: Artificial Sequence
<220> FEATURE:
<223> OTHER INFORMATION: TALE-R3

<400> SEQUENCE: 26
gaaccgccgt cttacgtaga gggtctctta atccgtgcgc ttggcac                     47

<210> SEQ ID NO 27
```

```
<210> SEQ ID NO 27
<211> LENGTH: 50
<212> TYPE: DNA
<213> ORGANISM: Artificial Sequence
<220> FEATURE:
<223> OTHER INFORMATION: TALE-F4

<400> SEQUENCE: 27
tttagcccgt accgtagcct aggtctcgat taaccccaga gcaggtcgtg           50

<210> SEQ ID NO 28
<211> LENGTH: 47
<212> TYPE: DNA
<213> ORGANISM: Artificial Sequence
<220> FEATURE:
<223> OTHER INFORMATION: TALE-R4

<400> SEQUENCE: 28
ttgcaccggt atcgtcgagg cggtctctaa gtccgtgcgc ttggcac              47

<210> SEQ ID NO 29
<211> LENGTH: 50
<212> TYPE: DNA
<213> ORGANISM: Artificial Sequence
<220> FEATURE:
<223> OTHER INFORMATION: TALE-F5

<400> SEQUENCE: 29
aagcatggat cgcaagggtt gggtctcgac ttaccccaga gcaggtcgtg           50

<210> SEQ ID NO 30
<211> LENGTH: 47
<212> TYPE: DNA
<213> ORGANISM: Artificial Sequence
<220> FEATURE:
<223> OTHER INFORMATION: TALE-R5

<400> SEQUENCE: 30
gggttgcgct cgcaattacc gggtctctaa ggccgtgcgc ttggcac              47

<210> SEQ ID NO 31
<211> LENGTH: 50
<212> TYPE: DNA
<213> ORGANISM: Artificial Sequence
<220> FEATURE:
<223> OTHER INFORMATION: TALE-F6

<400> SEQUENCE: 31
cgaaatccga ccggatgcct aggtctcgcc ttaccccaga gcaggtcgtg           50

<210> SEQ ID NO 32
<211> LENGTH: 47
<212> TYPE: DNA
<213> ORGANISM: Artificial Sequence
<220> FEATURE:
<223> OTHER INFORMATION: TALE-R6

<400> SEQUENCE: 32
gccatcgcgt cgcacgaagc tggtctctta gtccgtgcgc ttggcac              47

<210> SEQ ID NO 33
<211> LENGTH: 50
<212> TYPE: DNA
<213> ORGANISM: Artificial Sequence
<220> FEATURE:
<223> OTHER INFORMATION: TALE-F7

<400> SEQUENCE: 33
```

```
atagctggta gggctacggg cggtctcgac taaccccaga gcaggtcgtg            50
```

<210> SEQ ID NO 34
<211> LENGTH: 47
<212> TYPE: DNA
<213> ORGANISM: Artificial Sequence
<220> FEATURE:
<223> OTHER INFORMATION: TALE-R7

<400> SEQUENCE: 34

```
gaacgacccc tgacagtcgt tggtctctga gcccgtgcgc ttggcac               47
```

<210> SEQ ID NO 35
<211> LENGTH: 49
<212> TYPE: DNA
<213> ORGANISM: Artificial Sequence
<220> FEATURE:
<223> OTHER INFORMATION: TALE-F8

<400> SEQUENCE: 35

```
cgatatcgat cgccttacgc ggtctcggct caccccagag caggtcgtg             49
```

<210> SEQ ID NO 36
<211> LENGTH: 47
<212> TYPE: DNA
<213> ORGANISM: Artificial Sequence
<220> FEATURE:
<223> OTHER INFORMATION: TALE-R8

<400> SEQUENCE: 36

```
cgccacatat atagcgcgtc cggtctctta gcccgtgcgc ttggcac               47
```

<210> SEQ ID NO 37
<211> LENGTH: 49
<212> TYPE: DNA
<213> ORGANISM: Artificial Sequence
<220> FEATURE:
<223> OTHER INFORMATION: TALE-F9

<400> SEQUENCE: 37

```
gtgtgacggc tagcctagta ggtctcggct aaccccagag caggtcgtg             49
```

<210> SEQ ID NO 38
<211> LENGTH: 47
<212> TYPE: DNA
<213> ORGANISM: Artificial Sequence
<220> FEATURE:
<223> OTHER INFORMATION: TALE-R9

<400> SEQUENCE: 38

```
gcttgcggat cgatagcatg gggtctctga gtccgtgcgc ttggcac               47
```

<210> SEQ ID NO 39
<211> LENGTH: 27
<212> TYPE: DNA
<213> ORGANISM: Artificial Sequence
<220> FEATURE:
<223> OTHER INFORMATION: assem-F

<400> SEQUENCE: 39

```
tgttgtgtgg aattgtgagc ggataac                                     27
```

<210> SEQ ID NO 40
<211> LENGTH: 25
<212> TYPE: DNA

```
<213> ORGANISM: Artificial Sequence
<220> FEATURE:
<223> OTHER INFORMATION: assem-R

<400> SEQUENCE: 40
tgcaaggcga ttaagttggg taacg                                          25

<210> SEQ ID NO 41
<211> LENGTH: 4523
<212> TYPE: DNA
<213> ORGANISM: Artificial Sequence
<220> FEATURE:
<223> OTHER INFORMATION: pEF1a-NLS-TALE backbone-Fok1(R)-pA

<400> SEQUENCE: 41
gctgcttcgc gatgtacggg ccagatatac ggctccggtg cccgtcagtg ggcagagcgc      60
acatcgccca cagtccccga aagttgggg ggaggggtcg gcaattgaac cggtgcctag     120
agaaggtggc gcggggtaaa ctggaaagt gatgtcgtgt actggctccg cctttttccc      180
gagggtgggg gagaaccgta tataagtgca gtagtcgccg tgaacgttct ttttcgcaac     240
gggtttgccg ccagaacaca gctagcgttt aaacttaagc tgatccacta gtccagtgtg     300
gtggaattcg ccatggacta caaagaccat gacggtgatt ataaagatca tgacatcgat     360
tacaaggatg acgatgacaa gatggccccc aagaagaaga ggaaggtggg catccacggg     420
gtacccatgg tagatttgag aactttggga tattcacagc agcagcagga aaagatcaag     480
cccaaagtga ggtcgacagt cgcgcagcat cacgaagcgc tggtgggtca tgggtttaca     540
catgcccaca tcgtagcctt gtcgcagcac cctgcagccc ttggcacggt cgccgtcaag     600
taccaggaca tgattgcggc gttgccggaa gccacacatg aggcgatcgt cggtgtgggg     660
aaacagtgga gcggagcccg agcgcttgag gccctgttga cggtcgcggg agagctgaga     720
gggcctcccc ttcagctgga cacgggccag ttgctgaaga tcgcgaagcg gggaggagtc     780
acggcggtcg aggcggtgca cgcgtggcgc aatgcgctca cggagcacc cctcaacctg     840 accgagaccc tgacgccacc atggtgagca agggcgagga gctgttcacc ggggtggtgc     900
ccatcctggt cgagctggac ggcgacgtaa acggccacaa gttcagcgtg tccggcgagg     960
gcgagggcga tgccacctac ggcaagctga ccctgaagtt catctgcacc accggcaagc    1020
tgcccgtgcc ctggcccacc ctcgtgacca cctgaccta cggcgtgcag tgcttcagcc    1080
gctaccccga ccacatgaag cagcacgact tcttcaagtc cgccatgccc gaaggctacg    1140
tccaggagcg caccatcttc ttcaaggacg acggcaacta caagacccgc gccgaggtga    1200
agttcgaggg cgacaccctg gtgaaccgca tcgagctgaa gggcatcgac ttcaaggagg    1260
acggcaacat cctggggcac aagctggagt acaactacaa cagccacaac gtctatatca    1320
tggccgacaa gcagaagaac ggcatcaagg tgaacttcaa gatccgccac aacatcgagg    1380
acggcagcgt gcagctcgcc gaccactacc agcagaacac ccccatcggc gacggccccg    1440
tgctgctgcc cgacaaccac tacctgagca cccagtccgc cctgagcaaa gaccccaacg    1500
agaagcgcga tcacatggtc ctgctggagt tcgtgaccgc cgccgggatc actctcggca    1560
tggacgagct gtacaagtaa ggtctcaact cacgcctgag caggtagtgg ctattgcatc    1620
caatggaggg ggcagacccg cactggagtc aatcgtggcc cagctttcga ggccggaccc    1680
cgcgctggcc gcactcacta atgatcatct tgtagcgctg gcctgcctcg gcggacgacc    1740
cgccttggat gcggtgaaga agggctccc gcacgcgcct gcattgatta gcggaccaa    1800 cagaaggatt cccgagagga catcacatcg agtggcagga tcccagctgg tgaagagcga    1860
```

```
gctggaggag aagaagtccg agctgcggca caagctgaag tacgtgcccc acgagtacat    1920
cgagctgatc gagatcgcca ggaacagcac ccaggaccgc atcctggaga tgaaggtgat    1980
ggagttcttc atgaaggtgt acggctacag gggaaagcac ctgggcggaa gcagaaagcc    2040
tgacggcgcc atctatacag tgggcagccc catcgattac ggcgtgatcg tggacacaaa    2100
ggcctacagc ggcggctaca atctgcctat cggccaggcc gacgagatgc agagatacgt    2160
gaaggagaac cagaccccga ataagcacat caaccccaac gagtggtgga aggtgtaccc    2220
tagcagcgtg accgagttca agttcctgtt cgtgagcggc cacttcaagg caactacaa     2280 ggcccagctg accaggctga accacaaaac caactgcaat ggcgccgtgc tgagcgtgga    2340
ggagctgctg atcggcggcg agatgatcaa agccggcacc ctgacactgg aggaggtgcg    2400
gcgcaagttc aacaacggcg agatcaactt ctgataactc gagtctagag ggcccgttta    2460
aacccgctga tcagcctcga ctgtgccttc tagttgccag ccatctgttg tttgcccctc    2520
ccccgtgcct tccttgaccc tggaaggtgc cactcccact gtcctttcct aataaaatga    2580
ggaaattgca tcgcattgtc tgagtaggtg tcattctatt ctggggggtg gggtggggca    2640
ggacagcaag ggggaggatt gggaagacaa tagcaggcat gctggggatg cggtgggctc    2700
tatggcttct actgggcggt tttatggaca gcaagcgaac cggaattgcc agctggggcg    2760
ccctctggta aggttgggaa gccctgcaaa gtaaactgga tggctttctt gccgccaagg    2820
atctgatggc gcaggggatc aagctctgat caagagacag gatgaggatc gtttcgcatg    2880
attgaacaag atggattgca cgcaggttct ccggccgctt gggtggagag gctattcggc    2940
tatgactggg cacaacagac aatcggctgc tctgatgccg ccgtgttccg gctgtcagcg    3000
caggggcgcc cggttctttt tgtcaagacc gacctgtccg gtgccctgaa tgaactgcaa    3060
gacgaggcag cgcggctatc gtggctggcc acgacgggcg ttccttgcgc agctgtgctc    3120
gacgttgtca ctgaagcggg aagggactgg ctgctattgg gcgaagtgcc ggggcaggat    3180
ctcctgtcat ctcaccttgc tcctgccgag aaagtatcca tcatggctga tgcaatgcgg    3240
cggctgcata cgcttgatcc ggctacctgc ccattcgacc accaagcgaa acatcgcatc    3300
gagcgagcac gtactcggat ggaagccggt cttgtcgatc aggatgatct ggacgaagag    3360
catcacgggc tcgcgccagc cgaactgttc gccaggctca aggcgagcat gcccgacggc    3420
gaggatctcg tcgtgaccca tggcgatgcc tgcttgccga atatcatggt ggaaaatggc    3480
cgcttttctg gattcatcga ctgtgccggc tggtgtggcg gaccgctatc aggacatagc    3540
gttggctacc gtgatattgc tgaagagctt gcgcgaatgg ctgacgcttc tcgtgcttac    3600
ggtatcgccg cctcccgatg catcagtgca cttttcgggg aaatgtgcgc gaccctattt    3660 gtttatttt ctaatacatc aaatatgtat ccgctcatga caataaacc tgataaatgc      3720 ttcaataata gcacgtgcta aaacttcatt tttaatttta aaaggatcta ggtgaagatc    3780 cttttgata atctcatgac caaaatcctt aacgtgagt tttcgttcca ctgagcgtca     3840
gaccccgtag aaaagatcaa aggatcttct tgagatcctt ttttctgcg cgtaatctgc     3900 tgcttgcaaa caaaaaaacc accgctacca gcggtggttt gtttgccgga tcaagagcta    3960
ccaactcttt ttccgaaggt aactggcttc agcagagcg agataccaaa tactgttctt     4020
ctagtgtagc cgtagttagg ccaccacttc aagaactctg tagcaccgcc tacatacctc    4080
gctctgctaa tcctgttacc agtggctgct gccagtggcg ataagtcgtg tcttaccggg    4140
ttggactcaa gacgatagtt accggataag gcgcagcggt cgggctgaac ggggggttcg    4200
```

| | |
|---|---|
| tgcacacagc ccagcttgga gcgaacgacc tacaccgaac tgagatacct acagcgtgag | 4260 |
| ctatgagaaa gcgccacgct tcccgaaggg agaaaggcgg acaggtatcc ggtaagcggc | 4320 |
| agggtcggaa caggagagcg cacgagggag cttccagggg gaaacgcctg gtatctttat | 4380 |
| agtcctgtcg ggtttcgcca cctctgactt gagcgtcgat ttttgtgatg ctcgtcaggg | 4440 |
| gggcggagcc tatggaaaaa cgccagcaac gcggccttttt tacggttcct ggccttttgc | 4500 |
| tggccttttg ctcacatgtt ctt | 4523 |

<210> SEQ ID NO 42
<211> LENGTH: 5792
<212> TYPE: DNA
<213> ORGANISM: Artificial Sequence
<220> FEATURE:
<223> OTHER INFORMATION: pEF1a-NLS-TALE backbone-Fok1(L)-IRES-PURO-pA

<400> SEQUENCE: 42

| | |
|---|---|
| gctgcttcgc gatgtacggg ccagatatac gcgtggctcc ggtgcccgtc agtgggcaga | 60 |
| gcgcacatcg cccacagtcc ccgagaagtt ggggggaggg gtcggcaatt gaaccggtgc | 120 |
| ctagagaagg tggcgcgggg taaactggga agtgatgtc gtgtactggc tccgcctttt | 180 |
| tcccgagggt gggggagaac cgtatataag tgcagtagtc gccgtgaacg ttcttttttcg | 240 |
| caacgggttt gccgccagaa cacagagctc tctggctaac tagagaaccc actgcttact | 300 |
| ggcttatcga aattaatacg actcactata gctagcgttt aaacttaagc tgatccacta | 360 |
| gtccagtgtg gtggaattcg ccatggacta caaagaccat gacggtgatt ataaagatca | 420 |
| tgacatcgat tacaaggatg acgatgacaa gatggcccc aagaagaaga ggaaggtggg | 480 |
| catccacggg gtacccatgg tagatttgag aactttggga tattcacagc agcagcagga | 540 |
| aaagatcaag cccaaagtga ggtcgacagt cgcgcagcat cacgaagcgc tggtgggtca | 600 |
| tgggtttaca catgcccaca tcgtagcctt gtcgcagcac cctgcagccc ttggcacggt | 660 |
| cgccgtcaag taccaggaca tgattgccgg cttgccggaa ccacacatg aggcgatcgt | 720 |
| cggtgtgggg aaacagtgga gcggagcccg agcgcttgag gccctgttga cggtcgcggg | 780 |
| agagctgaga gggcctcccc ttcagctgga cacgggccag ttgctgaaga tcgcgaagcg | 840 |
| gggaggagtc acggcggtcg aggcggtgca cgcgtggcgc aatgcgctca cgggagcacc | 900 |
| cctcaacctg accgagaccc tgacgccacc atggtgagca agggcgagga gctgttcacc | 960 |
| ggggtggtgc ccatcctggt cgagctggac ggcgacgtaa acggccacaa gttcagcgtg | 1020 |
| tccggcgagg gcgagggcga tgccacctac ggcaagctga ccctgaagtt catctgcacc | 1080 |
| accggcaagc tgcccgtgcc ctggcccacc ctcgtgacca ccctgaccta cggcgtgcag | 1140 |
| tgcttcagcc gctaccccga ccacatgaag cagcacgact tcttcaagtc cgccatgccc | 1200 |
| gaaggctacg tccaggagcg caccatcttc ttcaaggacg acggcaacta caagacccgc | 1260 |
| gccgaggtga agttcgaggg cgacaccctg gtgaaccgca tcgagctgaa gggcatcgac | 1320 |
| ttcaaggagg acggcaacat cctggggcac aagctggagt acaactacaa cagccacaac | 1380 |
| gtctatatca tggccgacaa gcagaagaac ggcatcaagg tgaacttcaa gatccgccac | 1440 |
| aacatcgagg acggcagcgt gcagctcgcc gaccactacc agcagaacac ccccatcggc | 1500 |
| gacggccccg tgctgctgcc cgacaaccac tacctgagca cccagtccgc cctgagcaaa | 1560 |
| gaccccaacg agaagcgcga tcacatggtc ctgctggagt tcgtgaccgc cgccgggatc | 1620 |
| actctcggca tggacgagct gtacaagtaa ggtctcaact cacgcctgag caggtagtgg | 1680 |
| ctattgcatc caatggaggg ggcagacccg cactggagtc aatcgtggcc cagcttttcga | 1740 |

```
ggccggaccc cgcgctggcc gcactcacta atgatcatct tgtagcgctg gcctgcctcg   1800
gcggacgacc cgccttggat gcggtgaaga aggggctccc gcacgcgcct gcattgatta   1860
agcggaccaa cagaaggatt cccgagagga catcacatcg agtggcagga tcccagctgg   1920
tgaagagcga gctggaggag aagaagtccg agctgcggca caagctgaag tacgtgcccc   1980
acgagtacat cgagctgatc gagatcgcca ggaacagcac ccaggaccgc atcctggaga   2040
tgaaggtgat ggagttcttc atgaaggtgt acggctacag gggaaagcac ctgggcggaa   2100
gcagaaagcc tgacggcgcc atctatacag tgggcagccc catcgattac ggcgtgatcg   2160
tggacacaaa ggcctacagc ggcggctaca atctgcctat cggccaggcc gacgagatgg   2220
agagatacgt ggaggagaac cagacccgga ataagcacct caaccccaac gagtggtgga   2280
aggtgtaccc tagcagcgtg accgagttca agttcctgtt cgtgagcggc cacttcaagg   2340
gcaactacaa ggcccagctg accaggctga accacatcac caactgcaat ggcgccgtgc   2400
tgagcgtgga ggagctgctg atcggcgcg agatgatcaa agccggcacc ctgacactgg   2460
aggaggtgcg gcgcaagttc aacaacggcg agatcaactt cagatcttga taactcgagc   2520
ctctccctcc cccccccct aacgttactg gccgaagccg cttggaataa ggccggtgtg   2580
cgtttgtcta tatgttattt tccaccatat tgccgtcttt tggcaatgtg agggcccgga   2640
aacctggccc tgtcttcttg acgagcattc ctaggggtct ttcccctctc gccaaaggaa   2700
tgcaaggtct gttgaatgtc gtgaaggaag cagttcctct ggaagcttct tgaagacaaa   2760
caacgtctgt agcgaccctt tgcaggcagc ggaaccccc acctggcgac aggtgcctct   2820
gcggccaaaa gccacgtgta agatacac ctgcaaaggc ggcacaaccc cagtgccacg   2880
ttgtgagttg atagttgtg gaaagagtca aatggctctc ctcaagcgta ttcaacaagg   2940
ggctgaagga tgcccagaag gtaccccatt gtatgggatc tgatctgggg cctcggtaca   3000
catgctttac atgtgtttag tcgaggttaa aaaaacgtct aggccccccg aaccacgggg   3060
acgtggtttt cctttgaaaa acacgatgat aatatggcca aacccctcta gagccaccat   3120
gaccgagtac aagcccacgg tgcgcctcgc caccccgcgac gacgtcccca gggccgtacg   3180
caccctcgcc gccgcgttcg ccgactaccc cgccacgcgc cacaccgtcg atccggaccg   3240
ccacatcgag cgggtcaccg agctgcaaga actcttcctc acgcgcgtcg gctcgacat   3300 cggcaaggtg tgggtcgcgg acgacggcgc cgcggtggcg tctggacca cgccggagag   3360 cgtcgaagcg ggggcggtgt cgccgagat cggcccgcgc atggccgagt tgagcggttc   3420
ccggctggcc gcgcagcaac agatggaagg cctcctggcg ccgcaccggc caaggagcc   3480 cgcgtggttc ctggccaccg tcggcgtctc gcccgaccac caggggcaagg gtctgggcag   3540 cgccgtcgtg ctcccggag tggaggcggc cgagcgcgcc ggggtgcccg ccttcctgga   3600
aacctccgcg ccccgcaacc tccccttcta cgagcggctc ggcttcaccg tcaccgccga   3660
cgtcgaggtg cccgaaggac cgcgcacctg gtgcatgacc cgcaagcccg gtgcctgagg   3720
gcccgtttaa acccgctgat cagcctcgac tgtgccttct agttgccagc catctgttgt   3780
ttgcccctcc cccgtgcctt ccttgaccct ggaaggtgcc actcccactg tcctttccta   3840
ataaaatgag gaaattgcat cgcattgtct gagtaggtgt cattctattc tggggggtgg   3900
ggtggggcag gacagcaagg gggaggattg ggaagacaat agcaggcatg ctggggatgc   3960
ggtgggctct atggcttcta ctgggcggtt ttatggacag caagcgaacc ggaattgcca   4020
gctggggcgc cctctggtaa ggttgggaag ccctgcaaag taaactggat ggctttcttg   4080
```

| | |
|---|---:|
| ccgccaagga tctgatggcg caggggatca agctctgatc aagagacagg atgaggatcg | 4140 |
| tttcgcatga ttgaacaaga tggattgcac gcaggttctc cggccgcttg ggtggagagg | 4200 |
| ctattcggct atgactgggc acaacagaca atcggctgct ctgatgccgc cgtgttccgg | 4260 |
| ctgtcagcgc aggggcgccc ggttcttttt gtcaagaccg acctgtccgg tgccctgaat | 4320 |
| gaactgcaag acgaggcagc gcggctatcg tggctggcca cgacgggcgt tccttgcgca | 4380 |
| gctgtgctcg acgttgtcac tgaagcggga agggactggc tgctattggg cgaagtgccg | 4440 |
| gggcaggatc tcctgtcatc tcaccttgct cctgccgaga agtatccat catggctgat | 4500 |
| gcaatgcggc ggctgcatac gcttgatccg gctacctgcc cattcgacca ccaagcgaaa | 4560 |
| catcgcatcg agcgagcacg tactcggatg aagccggtc ttgtcgatca ggatgatctg | 4620 |
| gacgaagagc atcacgggct cgcgccagcc gaactgttcg ccaggctcaa ggcgagcatg | 4680 |
| cccgacggcg aggatctcgt cgtgacccat ggcgatgcct gcttgccgaa tatcatggtg | 4740 |
| gaaaatggcc gcttttctgg attcatcgac tgtgccggct ggtgtggcgg accgctatca | 4800 |
| ggacatagcg ttggctaccg tgatattgct gaagagcttg gcggaatggc tgaccgcttct | 4860 |
| cgtgcttacg gtatcgccgc ctcccgatgc atcagtgcac ttttcgggga aatgtgcgcg | 4920 |
| accctatttg tttatttttc taatacatca aatatgtatc cgctcatgag acaataacct | 4980 |
| gataaatgct tcaataatag cacgtgctaa aacttcattt ttaaatttaa aaggatctag | 5040 |
| gtgaagatcc ttttttgataa tctcatgacc aaaatccttt aacgtgagtt ttcgttccac | 5100 |
| tgagcgtcag acccgtaga aaagatcaaa ggatcttctt gagatccttt ttttctgcgc | 5160 |
| gtaatctgct gcttgcaaac aaaaaaacca ccgctaccag cggtggtttg tttgccggat | 5220 |
| caagagctac caactctttt tccgaaggta actggcttca gcagagcgca gataccaaat | 5280 |
| actgttcttc tagtgtagcc gtagttaggc caccacttca agaactctgt agcaccgcct | 5340 |
| acatacctcg ctctgctaat cctgttacca gtggctgctg ccagtggcga taagtcgtgt | 5400 |
| cttaccgggt tggactcaag acgatagtta ccggataagg cgcagcggtc gggctgaacg | 5460 |
| gggggttcgt gcacacagcc cagcttggag cgaacgacct acaccgaact gagatacc ta | 5520 |
| cagcgtgagc tatgagaaag cgccacgctt cccgaaggga gaaaggcgga caggtatccg | 5580 |
| gtaagcggca gggtcggaac aggagagcgc acgagggagc ttccaggggg aaacgcctgg | 5640 |
| tatctttata gtcctgtcgg gtttcgccac ctctgacttg agcgtcgatt tttgtgatgc | 5700 |
| tcgtcagggg ggcggagcct atggaaaaac gccagcaacg cggccttttt acggttcctg | 5760 |
| gccttttgct ggccttttgc tcacatgttc tt | 5792 |

<210> SEQ ID NO 43
<211> LENGTH: 538
<212> TYPE: DNA
<213> ORGANISM: Artificial Sequence
<220> FEATURE:
<223> OTHER INFORMATION: N-terminal of transcription activator-like
      effectors

<400> SEQUENCE: 43

| | |
|---|---:|
| atggactaca aagaccatga cggtgattat aaagatcatg acatcgatta caaggatgac | 60 |
| gatgacaaga tggcccccaa gaagaagagg aaggtgggca tccacggggt acccatggta | 120 |
| gatttgagaa ctttgggata ttcacagcag cagcaggaaa agatcaagcc caaagtgagg | 180 |
| tcgacagtcg cgcagcatca cgaagcgctg gtgggtcatg gtttacaca tgcccacatc | 240 |
| gtagccttgt cgcagcaccc tgcagccctt ggcacggtcg ccgtcaagta ccaggacatg | 300 |

```
attgcggcgt tgccggaagc cacacatgag gcgatcgtcg gtgtggggaa acagtggagc    360
ggagcccgag cgcttgaggc cctgttgacg gtcgcgggag agctgagagg gcctcccctt    420
cagctggaca cgggccagtt gctgaagatc gcgaagcggg gaggagtcac ggcggtcgag    480
gcggtgcacg cgtggcgcaa tgcgctcacg ggagcacccc tcaacctgac cgagaccc     538
```

```
<210> SEQ ID NO 44
<211> LENGTH: 257
<212> TYPE: DNA
<213> ORGANISM: Artificial Sequence
<220> FEATURE:
<223> OTHER INFORMATION: C-terminal of transcription activator-like
      effectors

<400> SEQUENCE: 44
```

```
ggtctcaact cacgcctgag caggtagtgg ctattgcatc caatggaggg ggcagacccg     60
cactggagtc aatcgtggcc cagctttcga ggccggaccc cgcgctggcc gcactcacta    120
atgatcatct tgtagcgctg gcctgcctcg gcggacgacc cgccttggat gcggtgaaga    180
aggggctccc gcacgcgcct gcattgatta agcggaccaa cagaaggatt cccgagagga    240
catcacatcg agtggca                                                   257
```

```
<210> SEQ ID NO 45
<211> LENGTH: 19
<212> TYPE: DNA
<213> ORGANISM: Artificial Sequence
<220> FEATURE:
<223> OTHER INFORMATION: Sequence-F

<400> SEQUENCE: 45
```

```
ctccccttca gctggacac                                                  19
```

```
<210> SEQ ID NO 46
<211> LENGTH: 18
<212> TYPE: DNA
<213> ORGANISM: Artificial Sequence
<220> FEATURE:
<223> OTHER INFORMATION: Sequence-R

<400> SEQUENCE: 46
```

```
agctgggcca cgattgac                                                   18
```

```
<210> SEQ ID NO 47
<211> LENGTH: 19
<212> TYPE: DNA
<213> ORGANISM: Artificial Sequence
<220> FEATURE:
<223> OTHER INFORMATION: Sequence 1

<400> SEQUENCE: 47
```

```
cgcgcgcgcg cgcgcgcgt                                                  19
```

```
<210> SEQ ID NO 48
<211> LENGTH: 17
<212> TYPE: DNA
<213> ORGANISM: Artificial Sequence
<220> FEATURE:
<223> OTHER INFORMATION: Sequence 2

<400> SEQUENCE: 48
```

```
cccactcccc atccagt                                                    17
```